(12) United States Patent
Burke et al.

(10) Patent No.: US 11,514,339 B2
(45) Date of Patent: Nov. 29, 2022

(54) MACHINE-LEARNING BASED RECOMMENDATION ENGINE PROVIDING TRANSPARENCY IN GENERATION OF RECOMMENDATIONS

(71) Applicant: Optum, Inc., Minnetonka, MN (US)

(72) Inventors: Christina Winans Burke, Arlington, VA (US); Daniel Mulcahy, Cambridge, MA (US); Mary Duncan, Washington, DC (US); Zhongjian Liu, Austin, TX (US)

(73) Assignee: Optum, Inc., Minnetonka, MN (US)

( * ) Notice: Subject to any disclaimer, the term of this patent is extended or adjusted under 35 U.S.C. 154(b) by 598 days.

(21) Appl. No.: 16/671,207

(22) Filed: Nov. 1, 2019

(65) Prior Publication Data

US 2020/0342335 A1 Oct. 29, 2020

Related U.S. Application Data

(60) Provisional application No. 62/837,826, filed on Apr. 24, 2019.

(51) Int. Cl.
*G16H 50/70* (2018.01)
*G06N 5/04* (2006.01)
(Continued)

(52) U.S. Cl.
CPC ........... *G06N 5/04* (2013.01); *G06F 16/9535* (2019.01); *G06N 20/00* (2019.01); *G06Q 40/08* (2013.01);
(Continued)

(58) Field of Classification Search
CPC ...... G06F 16/9535; G06N 5/04; G06N 20/00; G06Q 40/08; G06Q 10/10; G16H 10/60;
(Continued)

(56) References Cited

U.S. PATENT DOCUMENTS

2006/0202816 A1   9/2006   Crump et al.
2008/0059232 A1*  3/2008   Iliff .................. G16H 50/30
                                                     705/2
(Continued)

OTHER PUBLICATIONS

"Medicare Spending Per Beneficiary—Post-Acute Care Measures Public Comment Summary Report," Acumen, (160 pages), Mar. 2016, available online https://www.cms.gov/Medicare/Quality-Initiatives-Patient-Assessment-Instruments/Post-Acute-Care-Quality-Initiatives/Downloads/2016_03_24_mspb_pac_public_comment_summary_report.pdf.
(Continued)

*Primary Examiner* — Le H Luu
(74) *Attorney, Agent, or Firm* — Alston & Bird LLP

(57) ABSTRACT

Machine-learning based recommendation engines are configured to execute machine-learning models to generate recommendations as output for a user based at least in part on functional data received at the recommendation engine. The recommendation engine is further configured to automatically determine the relative importance of one or more functional data entries in generating the recommendation. Moreover, the recommendation engine executes additional machine-learning models, including a machine-learning model trained to avoid negative outcomes, and an opportunity-based machine-learning model to identify alternative recommendation options based on alternative training logic.

24 Claims, 13 Drawing Sheets

(51) Int. Cl.
*G16H 10/60* (2018.01)
*G06Q 40/08* (2012.01)
*G06F 16/9535* (2019.01)
*G06N 20/00* (2019.01)
*G16H 20/00* (2018.01)
*G16H 50/30* (2018.01)

(52) U.S. Cl.
CPC ............. *G16H 10/60* (2018.01); *G16H 20/00* (2018.01); *G16H 50/30* (2018.01); *G16H 50/70* (2018.01)

(58) Field of Classification Search
CPC ........ G16H 20/20; G16H 50/30; G16H 50/70; G16H 50/20; G16H 30/20; A61B 5/7275; G06H 15/00; H16H 40/60; H16H 40/67
See application file for complete search history.

(56) References Cited

U.S. PATENT DOCUMENTS

| | | | | |
|---|---|---|---|---|
| 2009/0171695 | A1* | 7/2009 | Cobbinah | G06Q 10/10 705/3 |
| 2010/0274584 | A1* | 10/2010 | Kim | G16H 15/00 704/9 |
| 2011/0303788 | A1 | 12/2011 | Amland et al. | |
| 2011/0313788 | A1 | 12/2011 | Amland et al. | |
| 2013/0096942 | A1 | 4/2013 | Bowles et al. | |
| 2013/0218053 | A1 | 8/2013 | Kaiser et al. | |
| 2014/0062694 | A1* | 3/2014 | Miladin | G16H 50/20 340/539.12 |
| 2014/0081658 | A1 | 3/2014 | Irving et al. | |
| 2014/0236612 | A1 | 8/2014 | Liberty | |
| 2015/0088628 | A1 | 3/2015 | Alhimiri | |
| 2015/0363568 | A1 | 12/2015 | Milo et al. | |
| 2015/0363569 | A1 | 12/2015 | Ryan et al. | |
| 2016/0004820 | A1* | 1/2016 | Moore | G16H 15/00 705/3 |
| 2016/0125143 | A1 | 5/2016 | Stadler et al. | |
| 2016/0188834 | A1 | 6/2016 | Erdmann et al. | |
| 2017/0262604 | A1* | 9/2017 | Francois | G16H 10/60 |
| 2017/0270260 | A1* | 9/2017 | Shetty | G16H 40/67 |
| 2017/0273600 | A1 | 9/2017 | Gubbi Lakshminarasimha et al. | |
| 2018/0342327 | A1* | 11/2018 | Madan | G16H 40/60 |
| 2018/0366225 | A1* | 12/2018 | Mansi | G16H 30/20 |
| 2018/0366229 | A1* | 12/2018 | Baronov | A61B 5/7275 |

OTHER PUBLICATIONS

Bowles, Kathryn H. et al. "Nurse Generated EHR Data Supports Post-Acute Care Referral Decision Making: Development and Validation of a Two-step Algorithm," AMIA Annual Symposium Proceedings, (Year: 2017), published online Apr. 16, 2018, pp. 465-474, PMID: 29854111; PMCID: PMC5977719, available online https://www.ncbi.nlm.nih.gov/pmc/articles/PMC5977719/.

Dobson, Allen|DaVanzo, Joan E. et al. "Clinically Appropriate and Cost-Effective Placement (CACEP): Improving Health Care Quality and Effficiency, Final Report," Alliance For Home Health Quality and Innovation, Nov. 9, 2012, (144 pages), available online http://www.ahhqi.org/images/pdf/cacep-report.pdf.

Jette, Diane U. et al. "AM-PAC '6-Clicks' Functional Assessment Scores Predict Acute Care Hospital Discharge Destination," Physical Therapy, vol. 94, No. 9, Sep. 1, 2014, pp. 1252-1261, available online https://doi.org/10.2522/ptj.20130359.

Jette, Diane U. et al. "Validity of the AM-PAC "6-Clicks" Inpatient Daily Activity and Basic Mobility Short Forms," Physical Therapy, vol. 94, Issue 3, Mar. 1, 2014, pp. 379-391, available online https://doi.org/10.2522/ptj.20130199.

Newhouse, Joseph P. et al. "Variation In Health Care Spending: Target Decision Making, Not Geography," Institute of Medicine of the National Academies, (207 pages), Oct. 1, 2013, available online https://www.ncbi.nlm.nih.gov/books/NBK201647/, ISBN-13: 978-0-309-28869-9ISBN-10: 0-309-28869-X.

\* cited by examiner

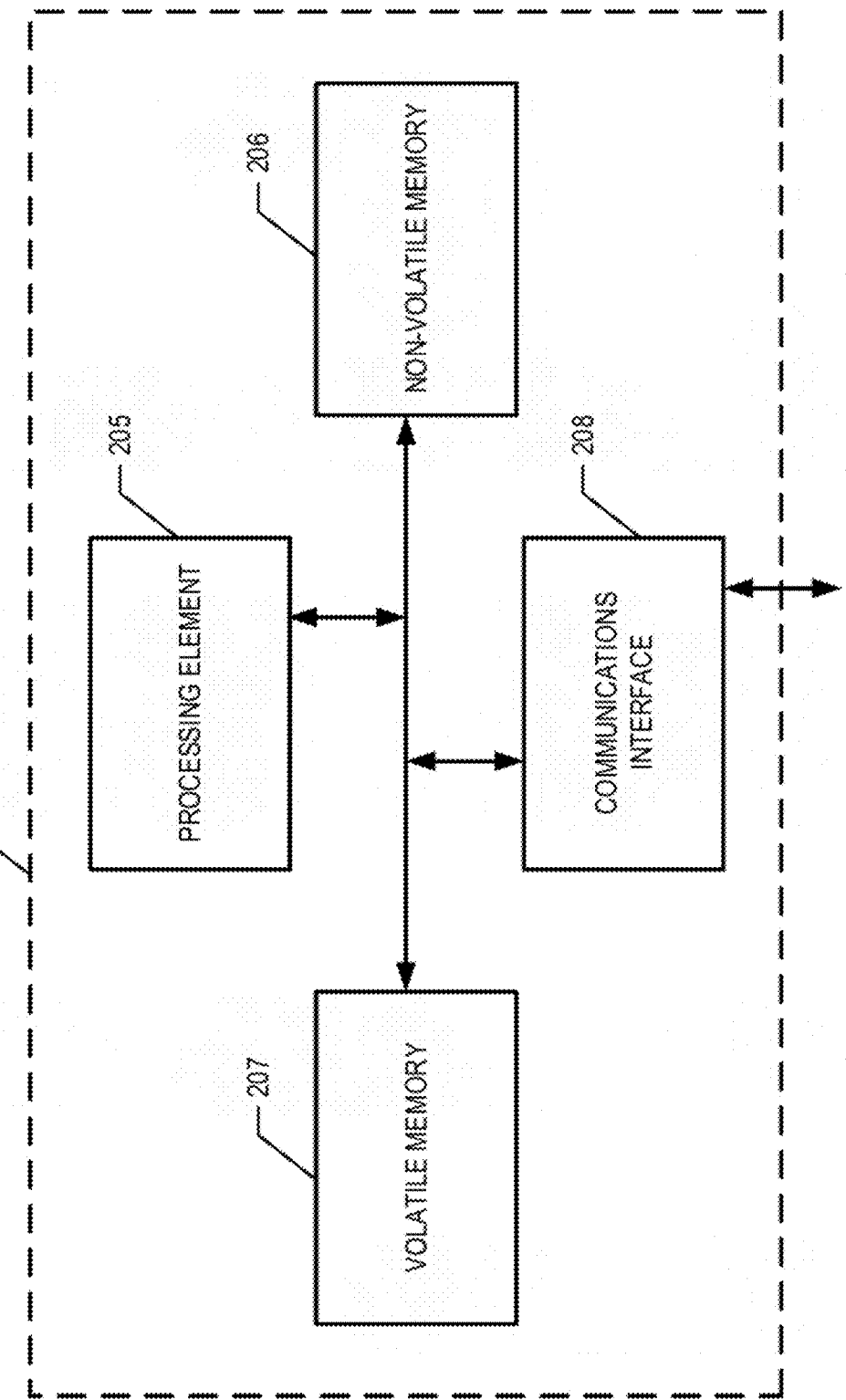

501 Receive functional data for patient to be discharged

502 Receive historical data

503 Determine most-utilized care type within historical data based on patient data

504 Determine patient data factors contributing to recommendation

505 Determine care outcome data for care types

506 Determine whether alternative care types have positive care outcomes

MACHINE-LEARNING BASED RECOMMENDATION ENGINE PROVIDING TRANSPARENCY IN GENERATION OF RECOMMENDATIONS

CROSS-REFERENCE TO RELATED APPLICATIONS

This patent application claims priority from U.S. Provisional Appl. Ser. No. 62/837,826, filed Apr. 24, 2019, which is incorporated herein by reference in its entirety.

TECHNOLOGICAL FIELD

Embodiments as discussed herein generally relate to machine-learning recommendation engines configured for generating recommendation scores for each of a plurality of available options, and for reverse engineering a plurality of subcomponents (e.g., scores of individual subcomponents) that contribute to the overall recommendation scores.

BACKGROUND

Historically, machine-learning based recommendation systems and methods have operated as black-box style tools that generally function to self-generate internal algorithms configured for generating a particular output, based on an input data set provided in a specific format. Often, little or no information can be gleaned from the recommendation, with the exception of a ranking of various options that are scored by the machine-learning recommendation system. Thus, users are generally unable to determine whether the machine-learning based recommendation system generated a recommendation based on suitable data for the specific circumstance under consideration. Moreover, it is generally difficult to determine whether the machine-learning based system introduced unacceptable forms of bias into the recommendation algorithm, without undertaking a resource intensive secondary analysis to estimate how a particular recommendation was generated.

Accordingly, a need exists for efficient systems and methods for automatically reverse engineering a machine-learning based recommendation to enable directed feature engineering of future iterations of the underlying machine-learning model and/or training data.

BRIEF SUMMARY

In general, embodiments of the present invention provide methods, apparatus, systems, computing devices, computing entities, and/or the like.

In accordance with one aspect, a computer-implemented method is provided for identifying contributing factors of a recommendation generated by a machine-learning recommendation engine. In certain embodiments, the method comprises: receiving functional data corresponding to a patient, wherein the functional data is linked with a patient medical record and wherein the functional data comprises a plurality of functional data entries; executing at least one machine-learning model to generate a recommendation for the patient based at least in part on functional data entries of the functional data; generating entry weights for one or more of the plurality of functional data entries within the functional data, wherein the entry weights are indicative of a relative importance of a corresponding functional data entry for generating the recommendation for the patient; and generating a graphical user interface identifying the recommendation and one or more of the plurality of functional data entries having corresponding entry weights satisfying a display criteria.

In various embodiments, executing at least one machine-learning model to generate a recommendation for the patient based at least in part on functional data comprises: executing a first machine-learning model to determine one or more options for the patient, wherein the first machine-learning model is trained to determine the one or more options according to common option utilization; and executing a second machine-learning model to determine rates of negative outcomes associated with the one or more options, wherein the second machine-learning model is trained via a negative training data set to avoid negative outcomes associated with one or more of the options.

In certain embodiments, the method further comprises executing an opportunity-based machine-learning model configured to determine one or more alternative options based at least in part on the functional data, wherein the one or more alternative options each embody a minority-utilized option for the patient; and wherein generating a graphical user interface further comprises generating a graphical user interface identifying the one or more alternative options. In accordance with certain embodiments, determining one or more alternative options comprises: identifying one or more options for the patient; identifying an outcome for each of the one or more options for the patient; identifying an option subset comprising one or more options determined to satisfy utilization criteria; identifying an outcome for each of one or more options for the patient; and determining one or more alternative options comprising options selected from the option subset determined to have an outcome at least matching the outcome for the recommendation.

In various embodiments, the recommendation comprises a post-acute care recommendation. Moreover, the machine-learning model may be embodied as an unsupervised training machine-learning model. In certain embodiments, the second machine-learning model is trained via negative training data to avoid options having negative outcomes. Moreover, in certain embodiments, receiving user input selecting the recommendation, wherein the recommendation is embodied as a post-acute care option; generating a prior-authorization approval for the recommendation; and transmitting data indicative of the prior-authorization approval to one or more computing entities.

Various embodiments are directed to an apparatus comprising at least one processor and at least one non-transitory memory comprising program code, wherein the at least one non-transitory memory and the program code are configured to, with the at least one processor, cause the apparatus to: receive functional data corresponding to a patient, wherein the functional data is linked with a patient medical record and wherein the functional data comprises a plurality of functional data entries; execute at least one machine-learning model to generate a recommendation for the patient based at least in part on functional data entries of the functional data; generate entry weights for one or more of the plurality of functional data entries within the functional data, wherein the entry weights are indicative of a relative importance of a corresponding functional data entry for generating the recommendation for the patient; and generate a graphical user interface identifying the recommendation and one or more of the plurality of functional data entries having corresponding entry weights satisfying a display criteria.

In certain embodiments, executing at least one machine-learning model to generate a recommendation for the patient based at least in part on functional data comprises: executing a first machine-learning model to determine one or more options for the patient, wherein the first machine-learning model is trained to determine the one or more options according to common option utilization; and executing a second machine-learning model to determine rates of negative outcomes associated with the one or more options, wherein the second machine-learning model is trained via a negative training data set to avoid negative outcomes associated with one or more of the options. In various embodiments, the at least one non-transitory memory and the program code are further configured to, with the at least one processor, cause the apparatus to: execute an opportunity-based machine-learning model configured to determine one or more alternative options based at least in part on the functional data, wherein the one or more alternative options each embody a minority-utilized option for the patient; and wherein generating a graphical user interface further comprises generating a graphical user interface identifying the one or more alternative options. In various embodiments, determining one or more alternative options comprises: identifying one or more options for the patient; identifying an outcome for each of the one or more options for the patient; identifying an option subset comprising one or more options determined to satisfy utilization criteria; identifying an outcome for each of one or more options for the patient; and determining one or more alternative options comprising options selected from the option subset determined to have an outcome at least matching the outcome for the recommendation. In certain embodiments, the recommendation comprises a post-acute care recommendation. Moreover, in various embodiments, the machine-learning model is embodied as an unsupervised training machine-learning model. In certain embodiments, the second machine-learning model is trained via negative training data to avoid options having negative outcomes. In various embodiments, the at least one non-transitory memory and the program code are further configured to, with the at least one processor, cause the apparatus to: receive user input selecting the recommendation, wherein the recommendation is embodied as a post-acute care option; generate a prior-authorization approval for the recommendation; and transmit data indicative of the prior-authorization approval to one or more computing entities.

Certain embodiments are directed to a non-transitory computer storage medium comprising instructions configured to cause one or more processors to: receive functional data corresponding to a patient, wherein the functional data is linked with a patient medical record and wherein the functional data comprises a plurality of functional data entries; execute at least one machine-learning model to generate a recommendation for the patient based at least in part on functional data entries of the functional data; generate entry weights for one or more of the plurality of functional data entries within the functional data, wherein the entry weights are indicative of a relative importance of a corresponding functional data entry for generating the recommendation for the patient; and generate a graphical user interface identifying the recommendation and one or more of the plurality of functional data entries having corresponding entry weights satisfying a display criteria.

In various embodiments, the non-transitory computer storage medium further comprises instructions configured to cause the one or more processors to execute a first machine-learning model to determine one or more options for the patient, wherein the first machine-learning model is trained to determine the one or more options according to common option utilization; and execute a second machine-learning model to determine rates of negative outcomes associated with the one or more options, wherein the second machine-learning model is trained via a negative training data set to avoid negative outcomes associated with one or more of the options.

In certain embodiments, the non-transitory computer storage medium further comprises instructions configured to cause the one or more processors to execute an opportunity-based machine-learning model configured to determine one or more alternative options based at least in part on the functional data, wherein the one or more alternative options each embody a minority-utilized option for the patient; and wherein generating a graphical user interface further comprises generating a graphical user interface identifying the one or more alternative options.

In various embodiments, determining one or more alternative options comprises: identifying one or more options for the patient; identifying an outcome for each of the one or more options for the patient; identifying an option subset comprising one or more options determined to satisfy utilization criteria; identifying an outcome for each of one or more options for the patient; and determining one or more alternative options comprising options selected from the option subset determined to have an outcome at least matching the outcome for the recommendation.

In various embodiments, the recommendation comprises a post-acute care recommendation. Moreover, in certain embodiments, the machine-learning model is embodied as an unsupervised training machine-learning model. In certain embodiments, the second machine-learning model is trained via negative training data to avoid options having negative outcomes. In various embodiments, the non-transitory computer storage medium further comprises instructions configured to cause the one or more processors to receive user input selecting the recommendation, wherein the recommendation is embodied as a post-acute care option; generate a prior-authorization approval for the recommendation; and transmit data indicative of the prior-authorization approval to one or more computing entities.

BRIEF DESCRIPTION OF THE SEVERAL VIEWS OF THE DRAWINGS

Reference will now be made to the accompanying drawings, which are not necessarily drawn to scale, and wherein:

FIG. 2A is a schematic of an analytic computing entity in accordance with certain embodiments of the present invention;

FIGS. 5A-5B illustrate a flow diagram of various steps associated with an example embodiment as discussed herein; and FIGS. 6-11 illustrate example user interfaces corresponding with various steps of an example embodiment as discussed herein.

DETAILED DESCRIPTION

Figure 1:
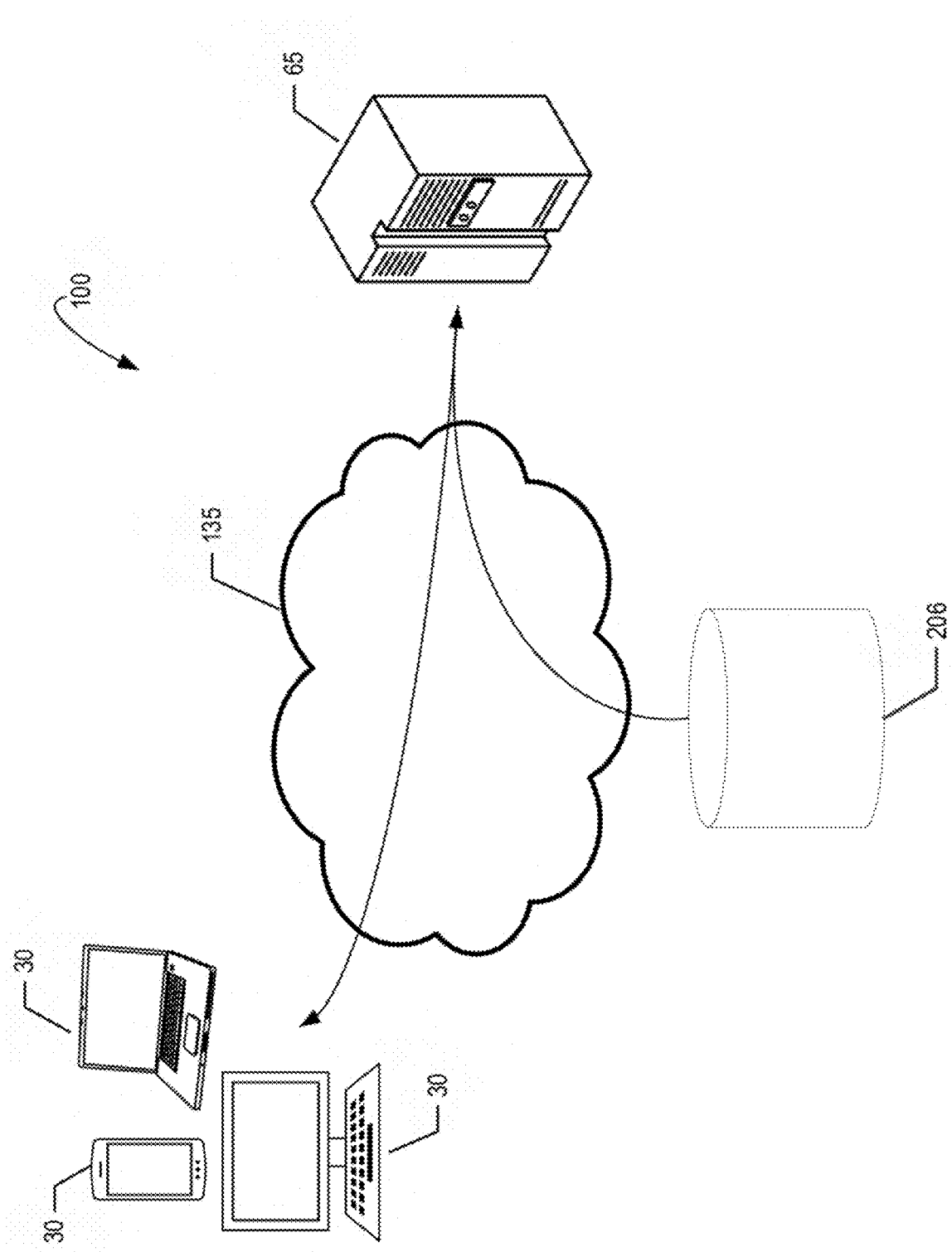
FIG. 1 is a diagram of a recommendation system that can be used in conjunction with various embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAIVI), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 1 provides an illustration of a recommendation system 100 that can be used in conjunction with various embodiments of the present invention. As shown in FIG. 1, the recommendation system 100 may comprise one or more analytic computing entities 65, one or more user computing entities 30, one or more memory storage areas 206, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

a. Exemplary Analytic Computing Entity

FIG. 2A provides a schematic of an analytic computing entity 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with other analytic computing entities 65, one or more user computing entities 30, and/or the like.

As shown in FIG. 2A, in one embodiment, the analytic computing entity 65 may include or be in communication with one or more processing elements 205 (also referred to as processors, processing circuitry, and/or similar terms used herein interchangeably) that communicate with other elements within the analytic computing entity 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the analytic computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like.

As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recommendation system may be stored. As a person of ordinary skill in the art would recognize, the information/data required for the operation of the recommendation system may also be partially stored in the cloud data storage system and partially stored in a locally maintained data storage system.

Memory media 206 may include information/data accessed and stored by the recommendation system to facilitate the operations of the system. More specifically, memory media 206 may encompass one or more data stores configured to store information/data usable in certain embodiments. For example, as shown in FIG. 2B, data stores encompassed within the memory media 206 may comprise functional data 211 (e.g., corresponding to a patient for which a care recommendation is sought), historical data 212 (e.g., comprising data indicative of historical treatment/care provided to one or more patients), provider data 213 (e.g., encompassing provider profiles for one or more providers and containing provider identifying data for each of the one or more providers), model data 214 (e.g., encompassing training data, algorithm data, and/or the like executable by the analytic computing entity 65 to generate recommendations in accordance with a machine-learning based system), and/or the like.

Figure 2B:
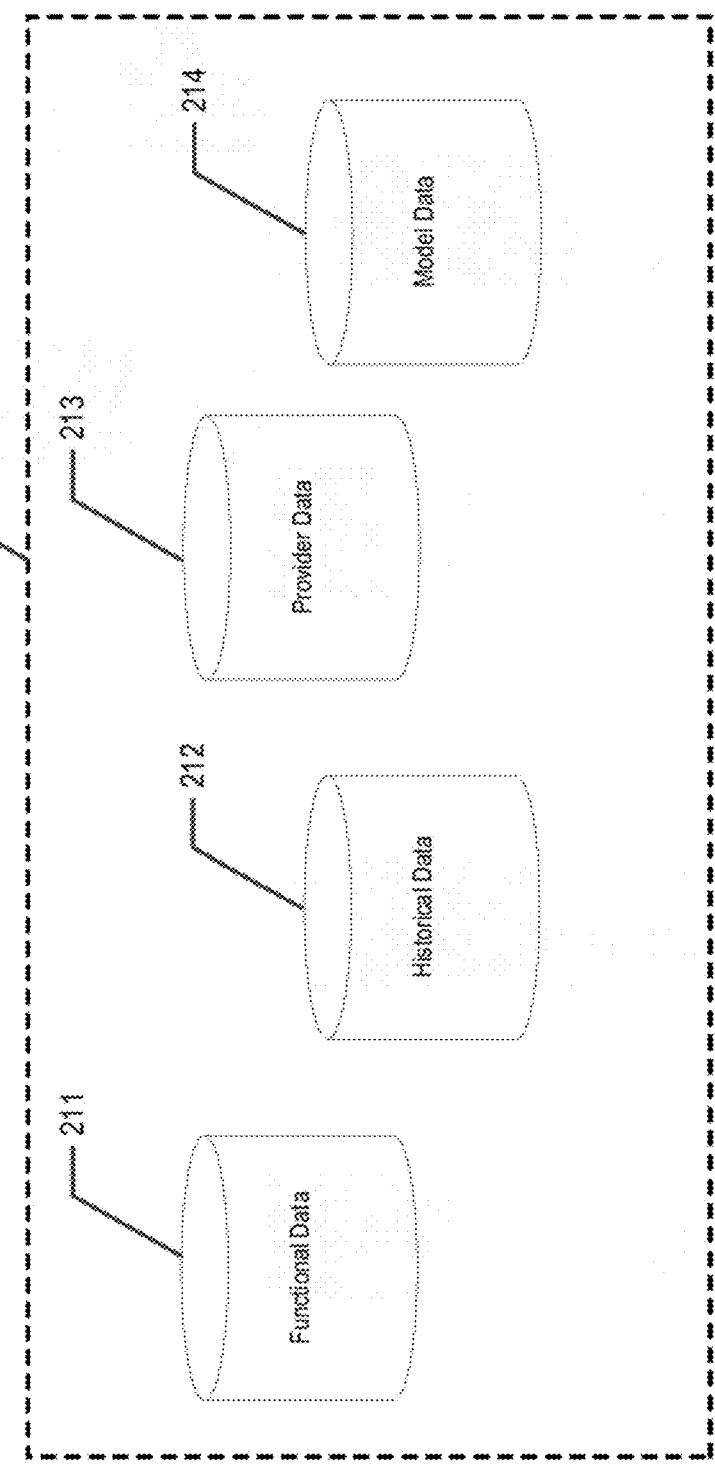
FIG. 2B is a schematic representation of a memory media storing a plurality of repositories, databases, data stores, and/or relational tables.

As illustrated in FIG. 2B, the memory media 206 may comprise functional data 211. The functional data 211 may be associated with patients' medical records, and the functional data 211 may be retrieved from one or more sources, such as from a user computing entity 30 (e.g., in such embodiments, at least a portion of the functional data 211 may be generated based at least in part on user input received at the user computing entity 30, for example entered by a provider (e.g., a physician) or a representative of a provider), an electronic medical record (EMR) system (e.g., which may be executable on a computing entity, such as a user computing entity 30, another analytic computing entity 65, and/or the like, at a remote location, such as at the location of a provider, at a cloud-based data storage area, and/or the like). In certain embodiments, the functional data 211 may comprise or otherwise identify one or more functional data entries, which may be embodied as patient identifying data, such as a unique patient identifier, a patient profile, and/or the like. The functional data 211 may comprise additional biographic data corresponding to the patient, such as the patient's name, social security number (if applicable), corresponding payer information (e.g., a payer name, a payer account uniquely associated with the patient, and/or the like), the patient's age and/or date-of-birth, the patient's contact information (e.g., the patient's phone number, physical residential address, mailing address, email address, social medial usernames/handles, and/or the like). Moreover, the functional data 211 may identify additional data regarding the particular circumstances for which a treatment/care recommendation may be requested, such as recent medical procedures provided to the patient (e.g., specifically for post-acute care recommendations), comorbidities of the patient, allergies of the patient, other conditions of the patient, prescriptions taken by the patient, and/or the like.

Continuing with FIG. 2B, the memory media 206 may comprise historical data 212. The historical data may comprise data associated with the particular patient for which a treatment/care recommendation is sought, and/or data associated with other patients. The historical data 212 of certain embodiments generally comprises functional data for which treatment/care has been provided previously (e.g., functional data such as that discussed above in reference to the current claim data), as well as data indicative of the treatment/care provided to the patient, and treatment/care outcomes for each patient. As just one example, the historical data may comprise complete and/or partial EMR data (including data from lab tests performed for patients (e.g., both tests performed and outcome of the tests performed), medications prescribed for patients (and outcomes associated with the prescribed medications), diagnoses, procedures, treatments, and/or the like. The data may be received from one or more separate systems (e.g., separate EMR systems) having differing data structures, and in such embodiments, the historical data may be normalized within the memory storage area 206. For example, the treatment/care outcomes may indicate a Length-of-Stay (LOS) within a care facility during which treatment/care was provided, whether the patient was readmitted following treatment/care for the same medical issue and/or a related medical issue, whether the patient perished following the treatment/care, and/or the like. As discussed in greater detail herein, the historical data may be utilized by the analytic computing entity 65 to determine whether the outcome of the treatment/care was positive (e.g., no readmission, minimal follow-up requirements and/or the like) or negative (e.g., death, readmission for related medical issues, extended treatment/care requirements, and/or the like).

Continuing with FIG. 2B, the memory media 206 may comprise provider data 213 indicative of one or more providers. Examples of providers include medical doctors, nurse practitioners, physician assistants, nurses, other medical professionals practicing in one or more of a plurality of medical specialties (e.g., psychiatry, pain management, anesthesiology, general surgery, emergency medicine, etc.), hospitals, urgent care centers, diagnostic laboratories, surgery centers, and/or the like. As noted above, the provider data 213 may comprise identifying data for each provider (e.g., a provider unique identifier, a provider name, a provider address, provider contact information (e.g., a provider phone number, a provider email address, a provider website, and/or the like). In certain embodiments, the provider data further comprises data indicative of the provider's specialty, services offered, availability, and/or the like. The provider data may be updated periodically (e.g., to reflect changing availability), such as in real-time, at defined intervals, and/or the like. In certain embodiments, at least a portion the provider data may be received from a user computing entity 30 associated with the provider (e.g., based at least in part on user input received at the user computing entity 30, and/or from additional analytic computing entities 65. In certain embodiments, the provider data may reflect data for providers without access to the analytic computing entity 65 and/or user interfaces associated with the recommendation engine and/or method as discussed herein. In such embodiments, the provider data may reflect data for providers that may be selected for providing additional treatment/care for patients, for example, for providing post-acute treatment for patients. Moreover, in certain embodiments, the provider data comprises data relating to providers having access to the analytic computing entity 65, and accordingly the provider data corresponding to these providers may comprise sign-in information for the provider (e.g., one or more user names and corresponding passwords for the provider and/or representatives of the provider).

In various embodiments, the provider profiles stored within the provider data 213 for various providers encompasses and/or identifies historical data corresponding to treatment/care provided by the provider for one or more patients (e.g., data within the historical data 212 may identify the provider(s) associated with the treatment/care, such that relevant historical data 212 may be linked or otherwise correlated with a provider profile within the provider data 213. In certain embodiments, the provider profile may comprise rankings, reviews, and/or other data identifying the competency of a particular provider in providing specific treatment/care for patients. Such data may be updated periodically for a provider (e.g., in real-time as new historical data is generated, at defined intervals, and/or the like). In other embodiments, data indicative of ratings, reviews, and/or the like may be generated in real-time for each treatment/care recommendation request, based on data stored within the provider profile at a time the treatment/care recommendation request is received at the analytic computing entity 65.

With reference again to FIG. 2B, the memory media 206 may comprise model data 214, such as data reflecting one or more algorithms, training data for one or more machine-learning models, and/or the like. The model data 214 may be generated and/or updated at the analytic computing entity 65, for example, as new historical data 212 is generated. In certain embodiments, the analytic computing entity 65 may be configured to utilize the historical data (or a portion thereof) as training data for one or more machine-learning model reflected within the model data. As discussed in greater detail herein, the model data 214 may comprise a general recommendation engine configured to generate, via machine-learning models, treatment/care recommendations for one or more patients based on functional data 211. Moreover, the model data 214 may comprise a reverse engineering engine for determining key features utilized for generating the treatment/care recommendation. In certain embodiments, the model data 214 may further comprise a provider recommendation engine for generating recommendations of one or more providers for providing the recommended treatment/care to the patient. As discussed above, provider recommendations may be generated in real-time based at least in part on the type of treatment/care recommended and/or the functional data 211. However, it should be understood that in certain embodiments, the provider recommendation may be generated based on the type of treatment/care recommended, without regard to the specific nuances of the functional data 211.

In one embodiment, the analytic computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 308. Thus, the databases, database instances, database management system entities, data, applications, programs, program modules, scripts, source code, object code, byte code, compiled code, interpreted code, machine code, executable instructions, and/or the like may be used to control certain aspects of the operation of the analytic computing entity 65 with the assistance of the processing element 205 and operating system.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with computing entities or communication interfaces of other analytic computing entities 65, user computing entities 30, and/or the like.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the analytic computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The analytic computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the analytic computing entity's components may be located remotely from other analytic computing entity 65 components, such as in a distributed system. Furthermore, one or more of the components may be aggregated and additional components performing functions described herein may be included in the analytic computing entity 65. Thus, the analytic computing entity 65 can be adapted to accommodate a variety of needs and circumstances.

b. Exemplary User Computing Entity

Figure 3:
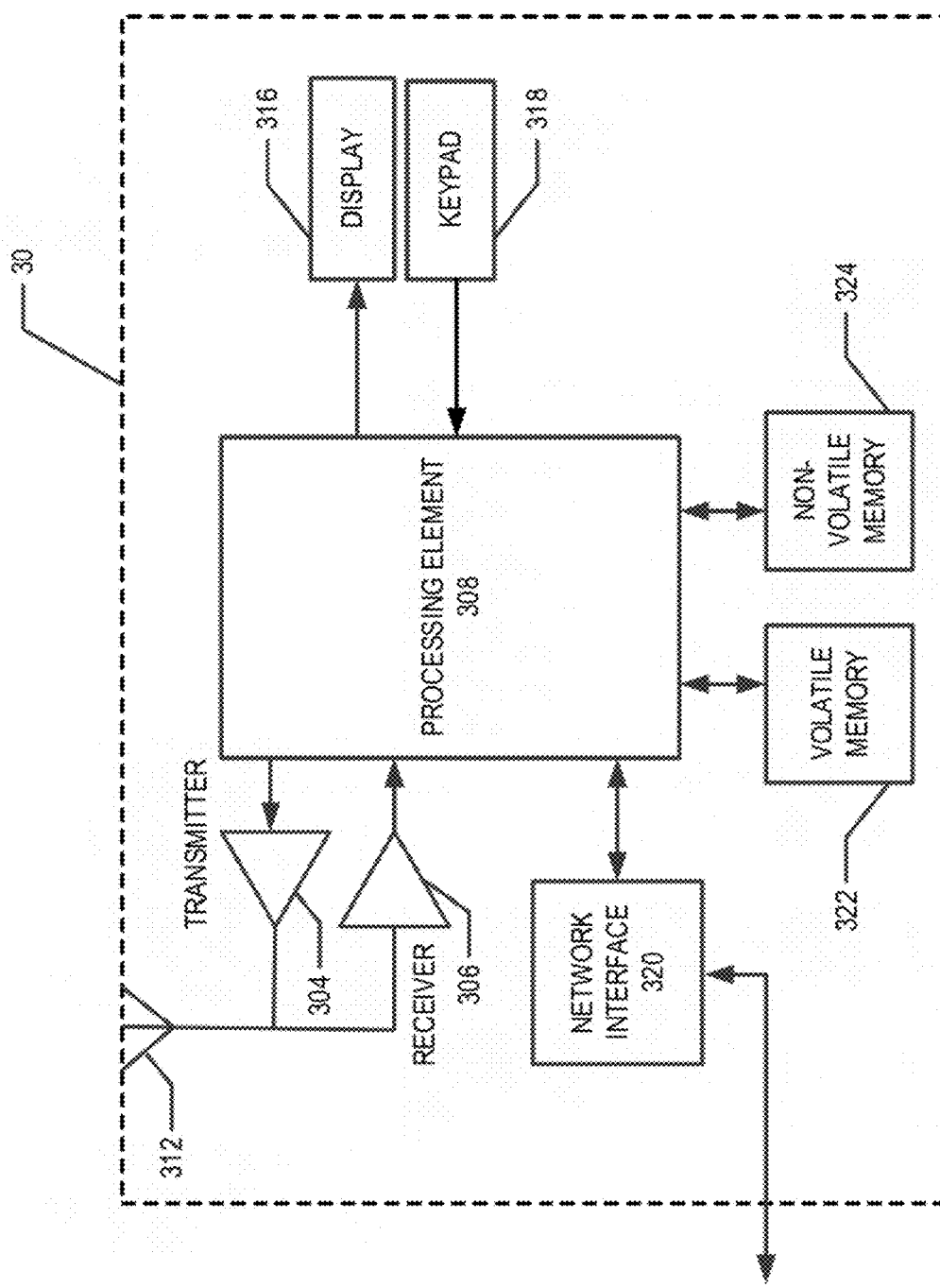
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity may be operated by an agent and include components and features similar to those described in conjunction with the analytic computing entity 65. Further, as shown in FIG. 3, the user computing entity may include additional components and features. For example, the user computing entity 30 can include an antenna 312, a transmitter 304 (e.g., radio), a receiver 306 (e.g., radio), a network interface 320, and a processing element 308 that provides signals to and receives signals from the transmitter 304 and receiver 306, respectively and/or the network interface 320. The signals provided to and received from the transmitter 304 and the receiver 306, respectively, may include signaling information/data in accordance with an air interface standard of applicable wireless systems to communicate with various entities, such as an analytic computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wired or wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including Radio-Frequency Identifier (RFID) tags, indoor beacons or transmitters, Wi-Fi access points, cellular towers, nearby computing devices (e.g., smartphones, laptops) and/or the like. For instance, such technologies may include iBeacons, Gimbal proximity beacons, Bluetooth Low Energy (BLE) transmitters, Near Field Communication (NFC) transmitters, and/or the like. These indoor positioning aspects can be used in a variety of settings to determine the location of someone or something to within inches or centimeters.

The user computing entity 30 may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the analytic computing entity 65. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. Exemplary System Operation

Figure 4:
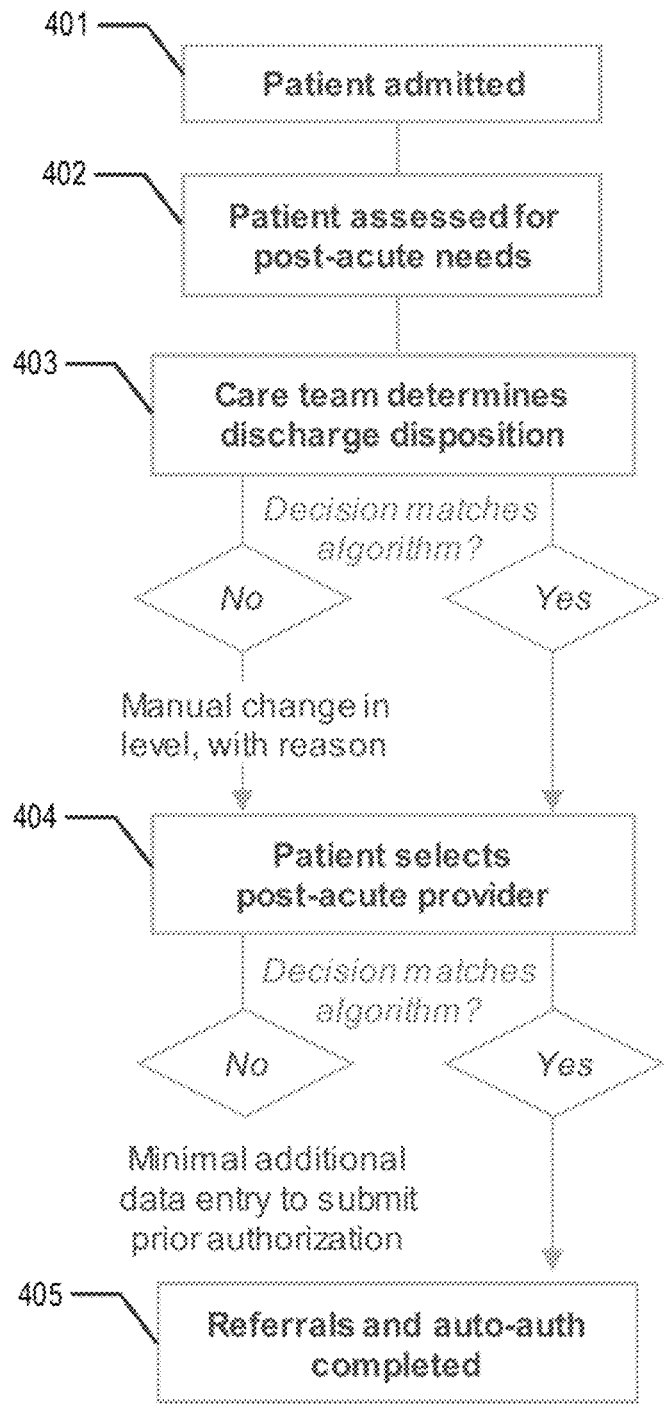
FIG. 4 illustrates a flow diagram of a specific implementation example incorporating embodiments discussed herein.

Reference will now be made to FIGS. 4-11. FIG. 4 provides an example workflow incorporating embodiments discussed herein. FIGS. 5A-5B illustrate an example flow diagram of a recommendation process according to one embodiment. FIGS. 6-11 illustrate example user interfaces according to certain embodiments.

a. Brief Overview

As indicated, there is a need for greater transparency in the operation of machine-learning based recommendation engines, both to provide confidence in the resulting recommendations given to users, and to facilitate additional feature engineering utilized to further refine the recommendation engine functionality and to provide recommendation results having increased precision. The need for greater transparency in the operation of machine-learning based recommendation engines has become evident within the healthcare field, for example, specifically when generating recommendations for post-acute care for patients, such as selecting between home-care, home health care, Skilled Nursing Facility (SNF) care, Inpatient Rehabilitation Facility (IRF) care, Long-Term Acute Care, and/or the like. For example, after a surgical procedure for a patient, a physician may have his/her own professional opinion as to how the patient should proceed with post-surgical care so as to maximize the likelihood of a complete recovery given the patient's unique characteristics and/or circumstances surrounding the surgery. However, a recommendation engine utilizing a machine-learning model for selecting a recommended post-acute care may identify a different recommended post-acute care treatment for the patient based on data made available to the analytic computing entity 65. To enable the provider to determine whether the recommended post-acute care recommended by the recommendation engine is appropriate for the patient, the analytic computing entity 65 of certain embodiments provides detailed information to the provider (e.g., via a graphical user interface displayed via a user computing entity 30 associated with the provider) regarding the features that influenced the machine-learning based recommendation engine determination of the provided post-acute care recommendation. Similarly, if it is determined that the recommendation engine is relying primarily on practically irrelevant data in generating recommendations, a user (e.g., an administrative user) may identify needed feature engineering for generating more accurate and precise recommendations through the machine-learning based recommendation engine.

Moreover, various embodiments maximize the amount of data that may be utilized by a machine-learning model both for training and classification/recommendation purposes within patient-data and/or current claim data, by extracting non-structured data that may be entered by a provider for a particular patient. Such features thereby maximize the amount of data that may be utilized when generating post-acute care recommendations for rare patient circumstances, to increase the precision and/or accuracy associated with generating post-acute care recommendations for those circumstances.

Certain embodiments utilize the recommendation engine to facilitate prior authorization processes for certain medical procedures. For example, after a provider requests a treatment/care recommendation, the analytic computing entity 65 generates a treatment/care recommendation for the provider to review. If the provider agrees, the provider (e.g., together with the patient) selects a care provider for providing the recommended treatment/care, and the analytic computing entity 65 then generates a prior authorization approval (e.g., comprising data indicating that a prior authorization has already been generated for a post-acute care treatment and/or comprising data indicating that formal prior authorization is not necessary for a post-acute care treatment), which may be provided to the provider, the selected care provider for the treatment/care, the patient, and/or the patient's payer. As a part of generating the prior authorization approval, the analytic computing entity 65 may be configured to determine a payer associated with the patient, determine applicable benefits for the patient in accordance with the patient's payer agreement, and determine requirements for generating the prior authorization approval in accordance with the patient's payer agreement. Moreover, as a part of generating the prior authorization approval, the analytic computing entity 65 may be configured to determine the estimated cost of the post-acute care, the estimated rate of negative outcomes (e.g., readmission) associated with the post-acute care, and/or the like when generating prior authorization for the post-acute care option.

Alternatively, if the provider does not agree with the recommendation as generated by the recommendation engine, the analytic computing entity 65 may still utilize data provided to the analytic computing entity 65 during the recommendation generation process to pre-populate at least a portion of a prior authorization form. For example, the analytic computing entity 65 may populate patient-specific data into a prior authorization form, payer-specific data into the prior authorization form, provider-data into the prior authorization form, and/or the like. The analytic computing entity 65 may be configured to accept user input from the provider for other portions of the prior authorization form (e.g., via a graphical user interface provided to the provider via a user computing entity 30). The provider may thus provide information such as the type of treatment/care requested, the care provider selected to provide the treatment/care, the reasoning for selecting the type of treatment/care requested, and/or the like. The analytic computing entity 65 may be configured thereafter to submit the prior authorization request form to the payer (or other appropriate computing entity) for approval.

Moreover, in certain embodiments the analytic computing entity 65 is configured to generate and/or store agreement statistics data indicative of the frequency with which providers agree with the recommended treatment/care provided by the recommendation engine of the analytic computing entity 65. The agreement statistics data may be compared with an accuracy criteria to determine whether the recommendations are relied upon at least a minimum frequency by providers/users. Upon determining that an accuracy criteria is satisfied, such as a determination that the frequency of providers agreeing with the recommended treatment/care falls below a threshold frequency (e.g., less than 75%, less than 50%, less than 30%, less than 20%, and/or the like), the analytic computing entity 65 may execute a remedial action, such as generating an alert (e.g., an alert indicating further feature engineering is needed to improve the accuracy/precision of the recommendation engine), analyzing the treatment/care selected for patients by particular providers (e.g., via a secondary machine-learning model), and/or the like to generate one or more new recommendation engines/models for generating treatment/care recommendations, and/or the like.

1. Technical Problem

A technical approach for providing additional, granular data regarding machine-learning based recommendations would provide additional confidence for users of the recommendation system. However, a technical problem exists for generating data indicative of features utilized for generating recommendations by a machine-learning model, because these machine-learning models are generally incapable of readily distinguishing between features utilized to generate an overall recommendation. Particularly as the complexity of machine-learning models increases (to address an increasing number of features, for example), the number of features relied upon to generate a recommendation increases, and by consequence the effect of each individual feature on the recommendation decreases. Thus, it becomes increasingly difficult to identify a small subset of features deemed relevant for presentation to a user as being important for establishing the recommendation. Moreover, because machine-learning models are only capable of generating recommendations based on features known to the analytic computing entity 65, determining which features are utilized for generating the recommendation enables a determination of needed new feature engineering for the machine-learning model to increase the accuracy of recommendations generated thereby.

2. Technical Solution

To overcome at least the above-identified technical challenges, a machine-learning based recommendation engine executing on an analytic computing entity is configured to generate recommendations based on input (e.g., current claim data) through a trained machine-learning model. Moreover, the machine-learning based recommendation engine further generates data indicative of one or more features within the input data that influenced the overall recommendation provided by the recommendation engine by reverse engineering the overall recommendation, utilizing the machine-learning model and related training data. Those features identified as being of particular importance in generating a recommendation are identified, such that they may be presented to a user for consideration. Moreover, various embodiments identify needed feature engineering in which particular recommendations are not relied upon by users, for example, when particular features are determined to be highly influential on the overall recommendation generated by the system.

b. Example Workflow Incorporating a Machine-Learning Based Recommendation Engine FIG. 4 illustrates an example workflow within which usage of a machine-learning based recommendation engine may be utilized to streamline an existing procedure. Specifically, the workflow of FIG. 4 exists within the context of a medical-related environment, in which a patient receives acute-treatment (e.g., a surgical procedure), for which some level of post-acute care is warranted. The workflow of FIG. 4 integrates usage of a machine-learning recommendation engine to aid in selection of appropriate post-acute care for a patient, and for generating any necessary prior authorization approvals prior to initiating the post-acute care.

Accordingly, as shown in FIG. 4, the overall workflow begins when a patient is admitted for acute care as reflected at step/operation 401. More specifically, the computer-related workflow incorporating usage of the machine-learning recommendation engine begins upon a computing system (e.g., a user computing entity 30 associated with a provider; an analytic computing entity 65; and/or the like) receiving functional data indicating that a particular patient has been admitted for acute care. As a specific example, an EMR system may receive functional data indicating that the patient has been admitted for acute care, and updated data (e.g., updated functional data and/or other data) may be provided to the EMR system throughout the patient's stay at the care facility (e.g., hospital). For example, data indicative of the outcome of the acute care may be provided to the EMR system; data indicative of the patient's condition after the acute care may be provided to the EMR system; and/or the like. Ultimately, as indicated at step/operation 402, the computing entity (e.g., which may be embodied as an EMR system) is utilized during an assessment of the patient for determination of appropriate post-acute care needs of the patient. For example, the assessment may determine whether the patient requires an extended hospitalization during the initial stages of post-acute care; whether the patient requires at least an at-home care supervisor assigned to the patient; whether the patient is sufficiently independent to warrant direct release to home, without any needed medical supervision; and/or the like.

Step/operation 403 of FIG. 4 represents the intersection between a provider's (of team of providers) professional opinion of a recommended post-acute care plan for a patient, and the usage of the machine-learning based recommendation engine to automatically generate a recommended post-acute care plan for a patient. Details regarding the process for generating a recommendation via the machine-learning based recommendation engine are discussed below. As reflected directly within step/operation 403, the provider (or collectively a plurality of providers generally forming a care team for the patient) determines a discharge disposition for the patient, including post-acute care recommendations for the patient. Separately, the recommendation engine generates its own set of post-acute care recommendations for the patient (also referred to herein as generating a patient classification, such as classifying a patient's eligibility for various post-acute care treatments) based at least in part on a machine-learning model.

Through a user interface (displayable via a display device of a user computing entity 30), the analytic computing entity 65 presents the provider/user with data indicative of the automatically generated recommendation/classification. If the provider/user agrees and selects a graphical user interface element indicating such agreement, the analytic computing entity 65 recognizes the provider's agreement, and presents the provider/user with another graphical user interface indicating one or more care providers recommended for providing the recommended level of post-acute care to the patient, as reflected at step/operation 404. The provider/user may then review the recommended post-acute care providers (which may be displayed in a ranking-based order (e.g., the highest-recommended/ranked provider displayed fist), in a distance-based order (e.g., the care provider located closest to the patient displayed first), and/or any other configuration) and select a particular recommended post-acute care provider for the patient. The analytic computing entity 65 may then receive the user input indicative of the selected post-acute care provider, and executes an automated prior authorization process for generating prior authorization data, such as by obtaining prior authorization from the patient's payer (e.g., in accordance with payer-defined processes) and/or determining that prior authorization is unnecessary, providing a referral to the selected post-acute care provider (and/or otherwise transmitting data indicating that prior authorization is unnecessary to the post-acute care provider), and providing a graphical user interface to the provider/user indicating confirmation of the completion of the prior authorization process, as indicated at step/operation 405.

However, if the provider/user disagrees with the automatically generated recommendation of post-acute care for the patient and/or the automatically selected recommended care providers for providing the post-acute care, and selects a graphical user interface indicating the provider's disagreement, the analytic computing entity 65 recognizes the provider's disagreement, and presents another graphical user interface enabling the provider to manually enter user input indicative of an alternative form of post-acute care (e.g., via free-text entry into a text box tagged as presenting free-text indicative of an alternative post-acute care, via selection of a plurality of presented options such as via a drop-down or a radio-button, and/or the like), as well as user input indicative of a reason for justifying the alternative form of post-acute care (e.g., via free-text entry into a text box tagged as presenting free-text indicative of a reason). In certain embodiments, the analytic computing entity 65 may be further configured to receive user input from the provider indicative of a requested care provider for providing the alternative post-acute care (e.g., via a drop-down, via free-text input, via a map-based interface, and/or the like). The user-provided data indicative of the requested alternative post-acute care may be utilized to generate a request for prior authorization for the alternative post-acute care, which may be routed from the analytic computing entity 65 to a payer (or other entity) for manual, semi-automatic, and/or automatic review thereof).

Although discussed above in the context of utilizing a machine-learning recommendation engine (executing on an analytic computing entity 65) for determining post-acute care recommendations for a patient, it should be understood that certain embodiments may be utilized for generating classifications/recommendations for a patient in other contexts, for example, based at least in part on the functional data associated with the patient.

c. Generating a Machine-Learning Based Recommendation

Figure 5B:
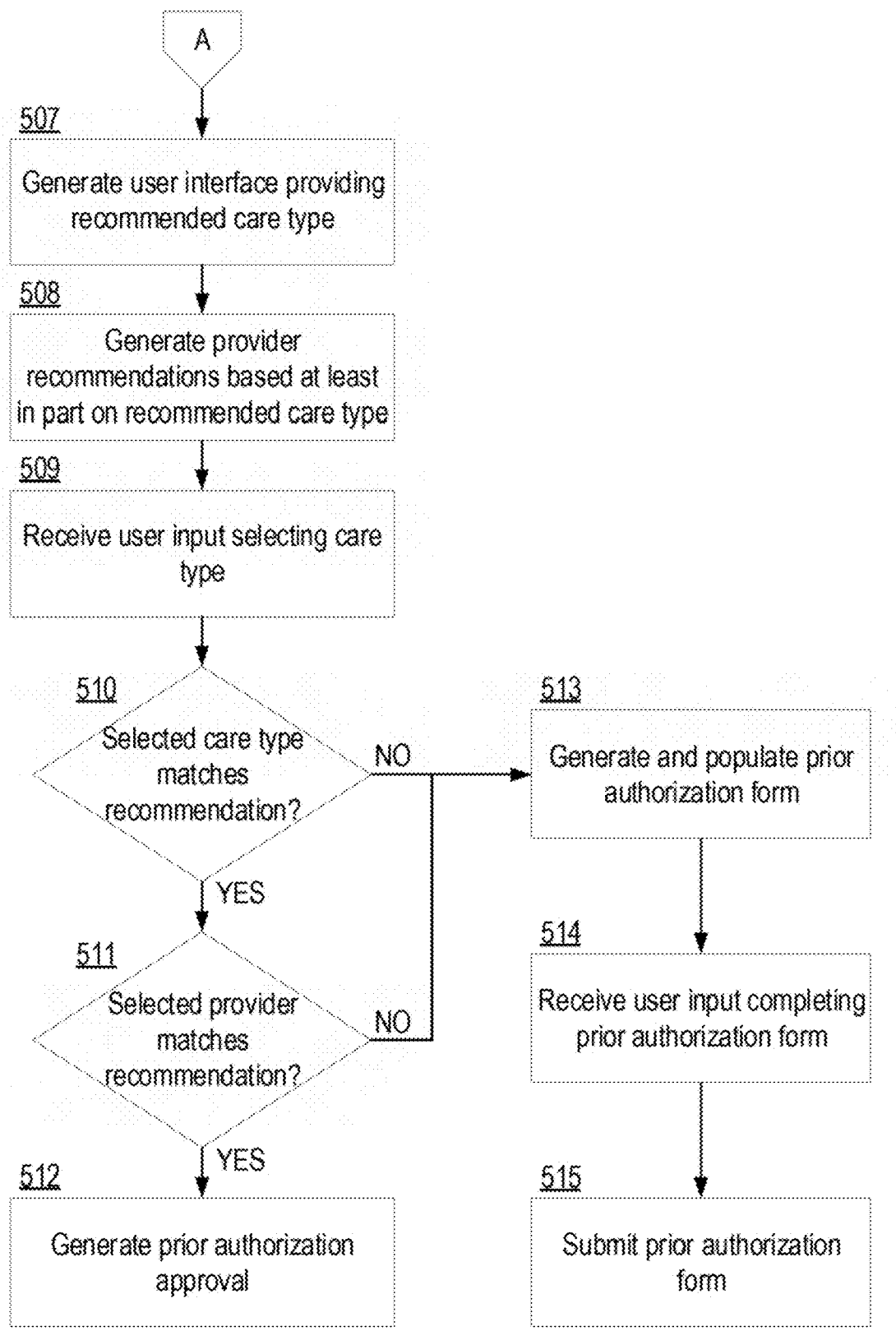
Figure 7:

FIGS. 5A-5B illustrate a flowchart showing example processes executed by an analytic computing entity 65 incorporating a machine-learning based recommendation engine. As alluded to above, certain processes illustrated in FIGS. 5A-5B overlap with portions of the workflow illustrated in FIG. 4. For example, the process illustrated in FIGS. 5A-5B may begin after a patient is admitted, after acute care is provided for the patient, and before/concurrently with a care team making an independent determination of a desired/recommended post-acute care treatment plan for the patient. It should be understood that certain processes discussed herein need not be performed in the order in which they are presented within the flowchart of FIGS. 5A-5B, and certain processes may be performed concurrently, or in an order different than what is presented herein.

As illustrated at step/operation 501 of FIG. 5A, the analytic computing entity 30 receives functional data for a patient to be discharged. The functional data may comprise current claim data indicative of one or more characteristics of a current claim, and/or at least a portion of the functional data may be retrieved based on data stored within the current claim data (e.g., utilizing a patient identifier within the current claim data to identify relevant functional data (e.g., within a functional database), and/or the like. As discussed herein, the functional data and/or the current claim data may comprise data identifying the patient, identifying one or more characteristics of the patient, identifying medical conditions of the patient, identifying the reason for admission for the patient, and/or the like. In certain embodiments, the functional data may additionally comprise provider notes regarding the patient (provider notes regarding the patient generally, provider notes regarding the patient's current admission, and/or the like). The functional data may comprise structured data, such as data having corresponding data tags indicative of the identity of each data item. In certain embodiments, the functional data may additionally comprise unstructured data, such as provider notes included within the functional data. The unstructured data may comprise a plurality of data points therein, however additional analysis may be required to retrieve those data points for further use.

In various embodiments, the analytic computing entity 65 is configured to utilize natural language processing (NLP) to retrieve portions of unstructured data, for example, from free-text entries provided by a user. The analytic computing entity 65 may extract data from clinical records for inclusion within current claim data and/or functional data, and the analytic computing entity 65 may thus generate structured data of current claim data and/or functional data (e.g., fielded data having defined values) based at least in part on data extracted from unstructured data portions (e.g., data extracted via NLP from one or more fielded data entries by a user) so as to provide a data set capable of comparison and/or machine-learning modelling so as to enable generation of machine-learning models for generating post-acute care recommendations.

The functional data and/or current claim data may be utilized as input for a machine-learning model for determining a post-acute care treatment recommendation for the patient. In certain embodiments, the analytic computing entity 65 may be configured to execute a plurality of machine-learning models each configured to determine one or more post-acute care options for a patient, and the analytic computing entity 65 may then identify a post-acute care treatment recommendation selected from the post-acute care options determined by the plurality of machine-learning models. As noted above, embodiments configured for usage of unstructured data within machine-learning models may thereby provide additional features that may be utilized to generate highly accurate and/or highly precise recommendations for post-acute care treatment. The machine-learning model may be generated based at least in part on historical data, received at the analytic computing entity 65 as indicated at step/operation 502.

The analytic computing entity 65 utilizes one or more training algorithms to train the one or more machine-learning models for determining post-acute care options and/or for determining a post-acute care recommendation for a patient. As just one example, the machine-learning model may be a clustering model (e.g., identifying similarities between the functional data associated with a current patient and historical data representing functional data of prior patients/claims), a technical consensus model, and/or the like. In certain embodiments, the analytic computing entity 65 may be configured to train a plurality of machine-learning models based at least in part on the historical data to (a) generate a machine-learning model configured to identify a post-acute treatment plan most-utilized by providers within the historical data for particular combinations of functional data/claim data, (b) generate a machine-learning model to identify features (and their respective values) deemed most relevant to determining the most-utilized post-acute treatment plan, (c) generate alternative post-acute treatment options for which a substantial minority of providers utilize, and which have outcomes as good as, or better than, the most-recommended post-acute care treatment, and/or (d) generate an overall post-acute care recommendation for the patient.

In certain embodiments, training may comprise supervised machine-learning or unsupervised machine-learning based at least in part on historical data. As just one example, a machine-learning model may be trained to determine at least one post-acute care option based at least in part on an engineered feature set generated based at least in part on input provided by feature engineering users (e.g., trained care providers capable of identifying those features that typically influence a decision to select a particular post-acute care option for a patient). It should be understood that certain embodiments may be configured to supplement an engineered feature set through machine-learning, as additional features are automatically identified as relevant for deciding an appropriate post-acute care option to be recommended for a particular patient.

In certain embodiments, each machine-learning model may utilize a different training regimen for generating and/or maintaining the corresponding machine-learning model. For example, a first machine-learning model for identifying a post-acute treatment plan that is commonly utilized by providers may utilize an unsupervised training regimen to identify post-acute care options. As an example, the machine-learning model may utilize a clustering model, a random forest model, a decision tree model, a neural network, a multivariate adaptive regression splines (MARS) model, a logistic regression model, and/or the like. The machine-learning model may utilize any of a variety of features for generating an appropriate algorithm for generating post-acute care recommendations. As just one example, a machine-learning model may utilize features such as: physician therapy and occupational therapy assessments (e.g., how much assistance does the patient require to ambulate), co-morbidities (e.g., dementia, obesity, behavioral), diagnoses (e.g., degenerative joint disease), visit (e.g., diagnosis-related group (DRG), length of stay), functional data (e.g., specifically, number of emergency department visits within a defined recent time period, age, and/or the like), readmission risks, source of admission, special care requirements (e.g., wound care, tracheotomy, and/or the like), lab values (e.g., metabolic panel), medications, social determinants (e.g., home caregiver status), and/or the like. It should be understood that a greater or fewer number of features may be considered.

In various embodiments, the machine-learning model is configured to generate recommendation scores for each of a plurality of post-acute care options based on various feature combinations of functional data/claim data. The generated recommendation scores are indicative of a relative level of how often a particular post-acute care option is utilized for particular patients having characteristics similar to those represented by the functional data/claim data, as evident by the historical data. Moreover, the machine-learning model (or a separate machine-learning model) may be configured to identify those specific features that most-impacted the determined recommendation score. For example, the machine-learning model may be configured to determine an entry weight for each feature utilized within the machine-learning model for determining a recommendation score, each feature being embodied as a functional data entry associated with the patient. Those features satisfying defined criteria (e.g., having an entry weight exceeding a threshold, a defined number of top features, identified based on entry weight, and/or the like) may be displayed to the user in certain embodiments.

In certain embodiments, the analytic computing entity 65 may be further configured to generate and/or maintain a machine-learning model for providing additional recognition of aspects of a post-acute care option, utilizing a training regimen to train against negative outcomes for post-acute care for patients. In certain embodiments, this training strategy may be integrated into the machine-learning model discussed above, or the analytic computing entity 65 may be configured to maintain a separate machine-learning model for generating additional data that may be considered when determining a post-acute care option for a patient. The analytic computing entity 65 may thus train the machine-learning model utilizing supervised machine-learning or unsupervised machine-learning based at least in part on historical data, including historical data indicative of outcomes deemed to be associated with a post-acute care option. As just one example, a training data set utilized with supervised machine-learning may be utilized to classify negative outcomes within the training dataset so as to validate the post-acute care option generated by the one or more machine-learning models as being an effective post-acute care option characterized by low levels of negative outcomes (e.g., death, readmission, extended care, infections, and/or the like).

As discussed in greater detail herein, the results of the machine-learning model for avoiding negative outcomes may be utilized in any of a variety of ways. As just one example, the results may be utilized to confirm whether the post-acute care option identified as being a commonly utilized post-acute care option by providers has a sufficiently low rate of negative outcomes (in such embodiments, the post-acute care option need not have the absolute lowest level of negative outcomes). In other embodiments, the results of the machine-learning outcome for avoiding negative outcomes may be utilized to select a post-acute care option having a lowest rate of negative outcomes (e.g., selected from a plurality of post-acute care options, such as a plurality of post-acute care options utilized by providers). In any event, the results of the machine-learning model for avoiding negative outcomes helps prevent an increase in the rate of negative outcomes, even when potentially reducing the level of post-acute care provided for patients. In other words, the results of the machine-learning model may be utilized to identify the minimum level of post-acute care needed by a patient so as to minimize the likelihood of a negative outcome for the patient. Moreover, because certain embodiments consider rates of infection as a negative outcome for a post-acute care option, these embodiments demonstrate that more resource intensive post-acute care levels, such as medically unnecessary admissions and/or over-utilization of medical care resources, may result in negative outcomes in certain cases.

In certain embodiments, an opportunity-based machine-learning model (e.g., which may be separate from the machine-learning models discussed above) may be utilized to identify one or more potentially innovative, alternative post-acute treatment options characterized as being utilized by a minority of providers and/or being utilized for a minority of patients having a particular set of characteristics (but for which a statistically significant amount of data exists so as to evaluate the effectiveness, rate of negative outcomes, and other outcomes associated with the post-acute treatment option), having a low rate of negative outcomes, having low medical resource usage (e.g., characterized by shorter treatment periods, incorporation of a less resource-intensive treatment (e.g., home care versus admitted patient care), and/or the like), and/or the like. To identify potentially innovative, alternative post-acute treatment plans, the opportunity-based machine-learning model may be trained with supervised or unsupervised learning to identify post-acute care options (e.g., a subset of all determined available post-acute care options) satisfying a utilization criteria, such as those post-acute care options utilized at least a threshold number of times (e.g., a statistically significant number of times) for patients having characteristics (represented by functional data associated with those patients) within a particular identified cluster and/or for patients having characteristics deemed sufficiently similar (e.g., by a machine-learning model). For the subset of post-acute care options determined to satisfy the utilization criteria, the opportunity-based machine-learning model as executed by the analytic computing entity 65 may be trained to determine outcomes associated with the post-acute care options, for example, by identifying post-acute care options having a rate of negative outcomes lower than the most-utilized post-acute care option, having a rate of positive outcomes higher than the most-utilized post-acute care option, having a lower medical resource usage than the commonly-utilized post-acute care option, and/or the like. As a specific example, the opportunity-based machine-learning model may be trained to identify post-acute care options having a lower medical resource usage than the most-utilized post-acute care option and having a rate of negative outcomes at least substantially equal to or lower than the most-utilized post-acute care option.

In various embodiments, the analytic computing entity 65 may be configured to periodically update the training data utilized to train each of the machine-learning models. For example, at defined intervals (e.g., nightly, weekly, monthly, quarterly, and/or the like), the analytic computing entity 65 may update the training data based at least in part on newly received historical data (e.g., current patient/current claim data may become historical data after treatment is completed and/or after a particular case has been closed for the patient. The analytic computing entity 65 may then retrain the one or more machine-learning models to reflect updated data reflecting outcomes for treatments provided to various patients.

With reference again to FIG. 5A, after training the various machine-learning models as discussed herein (which may occur prior to receipt of current patient/current claim data), the analytic computing entity 65 provides the current patient/current claim data as input to the one or more machine-learning models. Based on the input data comprising functional data and/or current claim data provided to the machine-learning models, the analytic computing entity 65 is configured to determine a most-utilized post-acute care option for the patient (as indicated at step/operation 503), utilizing the machine-learning models developed in accordance with the discussion provided herein. Moreover, as indicated at step/operation 504, the analytic computing entity 65 is configured to identify, within the input data, which features of the functional data and/or the current claim data most contributed to the identification of the particular post-acute care option by the machine-learning model.

Utilizing another machine-learning model, the analytic computing entity 65 is further configured to determine care outcome data for the determined post-acute care option identified by the recommendation engine, as well as for other alternative post-acute care options, as indicated at step/operation 505. At least a portion of the results of this determination may be presented to a user (as discussed herein via a graphical user interface). For example, presented data may be indicative of care outcomes may comprise average care outcomes, indicative of the likelihood of a negative outcome (e.g., the data may be displayed for different negative outcomes separately, such as providing data regarding the likelihood of death and data regarding the likelihood of readmission; or the data may be displayed for negative outcomes collectively, such as providing data regarding the likelihood of a negative outcome for a particular post-acute care option), and/or the like. In certain embodiments, the analytic computing entity 65 may be configured to determine whether any alternative post-acute care options (e.g., post-acute care options not identified as a recommended post-acute care option) have associated positive outcomes, as indicated at step/operation 506. In certain embodiments, a positive outcome may be identified as having a rate of negative outcomes below a defined threshold (e.g., less than 10% of patients develop a negative outcome). In other embodiments, a positive outcome may be identified as having a rate of negative outcomes at least substantially equal to or below a rate of negative outcomes associated with the recommended post-acute care option. In certain embodiments, the analytic computing entity 65 may be configured to generate a graphical user interface output upon identifying one or more alternative post-acute care options having positive outcomes. In other embodiments, if the analytic computing entity 65 does not identify any alternative post-acute care options having positive outcomes, the analytic computing entity 65 may not generate a graphical user interface output identifying the one or more alternative post-acute care options.

In certain embodiments, the analytic computing entity 65 may be further configured to limit results of alternative post-acute care options to those satisfying utilization criteria, such as being utilized by providers for treatment of patients having similar functional data/current claim data, so as to ensure that determinations of the likelihood of positive outcomes for alternative post-acute care options are only provided for those post-acute care options for which a statistically significant amount of data has been generated.

In certain embodiments, the analytic computing entity 65 is configured to identify one or more (e.g., one) post-acute care recommendation from the one or more identified post-acute care options determined by the plurality of machine-learning models. In certain embodiments, the analytic computing entity 65 may utilize a separate model (e.g., a machine-learning model, a rule-based model, and/or the like) to identify a post-acute care recommendation to be presented to a provider/user. As just one example, the analytic computing entity 65 may be configured to identify the post-acute care option having the lowest cost as the recommended post-acute care option. As another example, the analytic computing entity 65 may be configured to identify the post-acute care option having the lowest rate of negative outcomes as the recommended post-acute care option. As yet another example, the analytic computing entity 65 may be configured to utilize a model generated based at least in part on the cost of each post-acute care option and the rate of negative outcomes of each post-acute care option to identify a recommend post-acute care option. Other factors may additionally be utilized in determining a recommended post-acute care option.

Although it should be understood that the order of steps as illustrated in FIGS. 5A-5B may be changed, in certain embodiments (and as illustrated in FIGS. 5A-5B), the analytic computing entity 65 is configured to generate one or more graphical user interfaces to present the one or more post-acute care options to a user after determining rates of positive outcomes for one or more post-acute care options (e.g., the recommended post-acute care option and one or more alternative post-acute care options). In certain embodiments, the analytic computing entity 65 may be configured to present the post-acute care option identified by a first machine-learning model (e.g., identifying a most-utilized post-acute care option) for a user if no alternative post-acute care options have positive outcomes. However, if one or more alternative post-acute care options are identified as having positive outcomes, the analytic computing entity 65 may present a graphical user interface presenting the one or more alternative post-acute care options for selection by the user. Particular for those embodiments in which the positive outcomes of the alternative post-acute care options are more attractive than the most-utilized post-acute care option, the analytic computing entity 65 may not present the most-utilized post-acute care option, or the analytic computing entity 65 may present the most-utilized post-acute care option, without providing the user with an option to select the most-utilized post-acute care option.

As indicated above, the graphical user interface provided to the user may be configured to receive user input selecting a post-acute care option. In certain embodiments, the graphical user interface may be configured to receive user input selecting a post-acute care option of a plurality of available post-acute care options. In other embodiments, selection of a post-acute care option may comprise selecting a user interface element indicating that the user agrees with a single recommendation for a post-acute care option presented to the user.

Upon receipt of user input selecting a post-acute care option, the analytic computing entity 65 may be configured to identify one or more provider recommendations for providing the patient with the selected post-acute care. Generation of a provider recommendation according to certain embodiments comprises determining a provider recommendation based at least in part on functional data, current claim data, and/or the selected post-acute care option. In certain embodiments, the analytic computing entity 65 may be configured to execute a machine-learning model for determining one or more provider recommendations. In certain embodiments, the machine-learning model may be configured to generate overall recommendations for providers treating patients having similar functional data and/or current claim data utilizing the selected post-acute care option. The machine-learning model may be configured to identify those providers having positive care outcomes, low cost, and/or a combination of provider characteristics satisfying corresponding requirements. The machine-learning model may be configured to generate provider scores. The analytic computing entity 65 may then be configured to review the scored providers to determine providers within a defined distance of the patient's location (and/or the provider's location, in certain embodiments). The analytic computing entity 65 may then be configured to identify one or more providers within the defined distance of the patient's location and/or the provider's location that satisfy applicable scoring criteria for providing the selected post-acute care. For example, the analytic computing entity 65 may be configured to select the highest ranked providers satisfying the applicable distance criteria (e.g., the 10 highest ranked providers, the 5 highest ranked providers, and/or the like). The listing of providers may be further limited based at least in part on provider-specified availability. Those providers indicating (e.g., via manual data entry to the analytic computing entity 65 via a provider portal or via automatic determinations of availability based at least in part on a calendar or other scheduling data made available by the provider) that there is no availability for new patients may be excluded from any listing of recommended providers.

The analytic computing entity 65 may be configured to provide the generated provider recommendations within a graphical user interface presented to a user for selection of a provider for the patient's post-acute care. In certain embodiments, the graphical user interface may be configured to enable the user to select only from a displayed listing encompassing the generated provider recommendations. In other embodiments, the graphical user interface may provide a user with options to select one of the providers of the generated provider recommendations or to identify and/or select a provider that is not included in the listing of recommended providers. In certain embodiments, the graphical user interface may be configured to accept free-text user input selecting a particular provider not included within the listing of generated provider recommendations. In other embodiments, the graphical user interface may present a listing of non-recommended (or providers not otherwise included within a listing of recommended providers) providers, from which a user may select.

In certain embodiments, upon the user providing user input selecting recommended provider for the selected post-acute care option, the analytic computing entity 65 may be configured to generate prior authorization approval for the post-acute care treatment, as indicated at step/operation 512. In certain embodiments, the prior authorization approval may comprise data indicating that a prior authorization has been received from a payor, or the prior authorization approval may comprise data indicating that a prior authorization is not needed for the post-acute care. The generated prior authorization approval may comprise a prior authorization confirmation identifier (e.g., a unique number), data indicating the provider from which the authorization is provided, the post-acute care to be provided, the provider to be providing the post-acute care, a date and/or time stamp, and/or the like.

In certain embodiments, generating prior authorization comprises generating data necessary for a payer to approve the post-acute care option selected and/or generating data indicating that a prior authorization is unnecessary. Moreover, generating a prior authorization may additional comprise generating data necessary for providing the selected provider with evidence identifying the prior authorization approval. In certain embodiments, the analytic computing entity 65 may be configured to query functional data to determine a payer associated with the patient. Based on the identified payer, the analytic computing entity 65 determines an electronic contact information for the payer and transmits a query to the payer's computing systems to determine what information is necessary for inclusion with the prior authorization data to be provided to the payer and/or to the provider. The analytic computing entity 65 may then receive data from the payer computing entity identifying the data necessary (and data formatting necessary) for inclusion within the prior authorization data to be provided to the payer and/or the provider. In other embodiments however, the analytic computing entity 65 may store payer data indicating the data types necessary (and data formatting necessary) for prior authorization. In certain embodiments, the analytic computing entity 65 may then be configured to provide data to the payer computing system (including the data identified as necessary and provided in the data format specified by the payer computing entity). Prior to proceeding, the analytic computing entity 65 of certain embodiments may be configured to await receipt of approval data from the payer computing entity. However, in other embodiments, the analytic computing entity 65 may be configured to automatically proceed to provide prior authorization data to the selected provider. The prior authorization data transmitted to a provider may comprise the prior authorization unique identifier, data identifying the patient, data identifying the post-acute care to be provided, and/or the like. Moreover, the analytic computing entity 65 may be configured to store the generated prior authorization data in memory for later retrieval and usage.

In certain embodiments, a payor may provide approval criteria data that may be utilized by the analytic computing entity 65 to identify circumstances in which a prior authorization is unnecessary for particular post-acute care options (and in such cases, the prior authorization approval is embodied as data indicating that a prior authorization is unnecessary). The approval criteria may be dynamic in certain embodiments and may be embodied as a machine-learning model configured to determine whether prior authorization is necessary for a particular post-acute care option.

As just one example, determining whether prior authorization is necessary begins by determining a percentage of patients of a particular patient type (e.g., having characteristics represented by functional data determined to be similar) that received each of one or more post-acute care options, historically. A rate of negative outcomes is determined for the one or more post-acute care options based at least in part on the historical data. In certain embodiments, a level of statistical significance is further determined for the rate of negative outcomes.

Those post-acute care options that do not satisfy the utilization criteria discussed above (e.g., indicating usage of the post-acute care option for at least a minimum number of times for a particular patient type) and/or that have a minimum rate of negative outcomes may be identified as requiring prior authorization. Thus, for users/providers selecting one of these post-acute care options, the analytic computing entity 65 may be configured to require the user/provider to submit a prior authorization request form before receiving approval.

For those post-acute care options that satisfy the utilization criteria and have a rate of negative outcomes below the defined minimum rate of negative outcomes, the analytic computing entity 65 may be configured to identify the post-acute care option having the lowest predicted cost of care (e.g., as determined based at least in part on historical data) and/or having the lowest rate of negative outcomes (e.g., as determined based at least in part on historical data). The identified post-acute care option may be identical to the recommend post-acute care option identified above.

In certain embodiments, if no post-acute care options are determined to be characterized by the lowest predicted cost of care and the lowest rate of negative outcomes, the analytic computing entity 65 may be configured to identify the most-utilized post-acute care option. Again, the identified post-acute care option may be identical to the recommended post-acute care option identified above.

The analytic computing entity 65 may be configured to determine that the post-acute care option identified as characterized by the lowest predicted cost of care and the lowest rate of negative outcomes, or the post-acute care option identified as being the most-utilized post-acute care option, is the a recommended post-acute care option, for which prior authorization is not needed before generating the prior-authorization approval.

As shown in FIG. 5B, if a user selects a post-acute care option that does not match options provided by the analytic computing entity 65 (e.g., a recommended post-acute care option and/or an alternative post-acute care option determined to have positive outcomes), and/or if the user selects a non-recommended provider, the analytic computing entity 65 may provide a graphical user interface to the user indicating that prior authorization must be completed through traditional channels, such as the submission of a prior authorization form to be reviewed, at least in part, manually by a payer. As indicated in steps/operations 513-515, the analytic computing entity 65 may be configured to aid a user in generating a prior authorization approval form to be submitted to the payer. Similar to the process for generating prior authorization approval as discussed above, the analytic computing entity 65 may be configured to query a payer computing entity after determining a relevant payer based on functional data, to determine data necessary for inclusion within a prior authorization form and/or for determining an appropriate format for the prior authorization form.

The analytic computing entity 65 may be further configured to pre-populate at least a portion of a prior authorization form for the user, based at least in part on functional data, provider data (for the provider generating the prior authorization request), and/or user input provided to the analytic computing entity 65. For example, portions of the prior authorization form may be populated based at least in part on user input selecting a particular post-acute care option requested for the patient, a provider requested to provide the post-acute care option for the patient, and/or the like. The analytic computing entity 65 may be further configured to receive user input (e.g., within a fielded data entry graphical user interface) indicative of additional data required for the prior authorization form. As just one example, the analytic computing entity 65 may be configured to receive user input (e.g., free-text user input) providing a reason for requesting a deviation from the recommendations for post-acute care provided by the analytic computing entity 65.

Upon completion of the prior authorization form, the analytic computing entity 65 may be configured to transmit the prior authorization form to the payer for review.

d. Example Implementation

Figure 11:
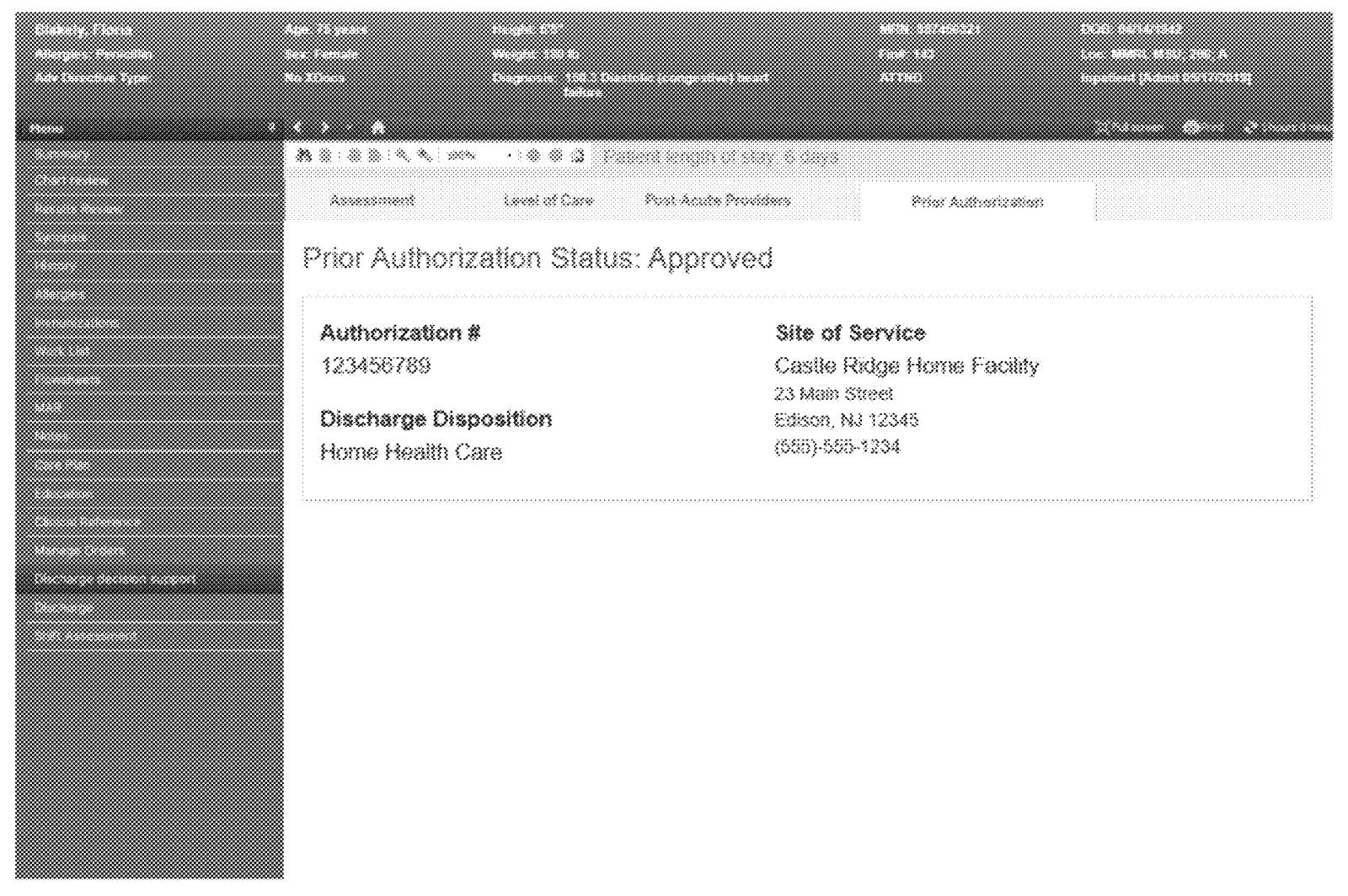

FIGS. 6-11 provide screenshots of example user interface screens that may be generated by an analytic computing entity 65 and/or presented to a user (e.g., via a user computing entity 30). In certain embodiments, the example user interface screens may be incorporated within and/or accessible via a provider office management program (e.g., an EMR program). However, in other embodiments the example user interface screens may be accessible via a standalone computer software system executable via the user computing entity 30 and/or based at least in part on data generated by the analytic computing entity 65.

Figure 6:
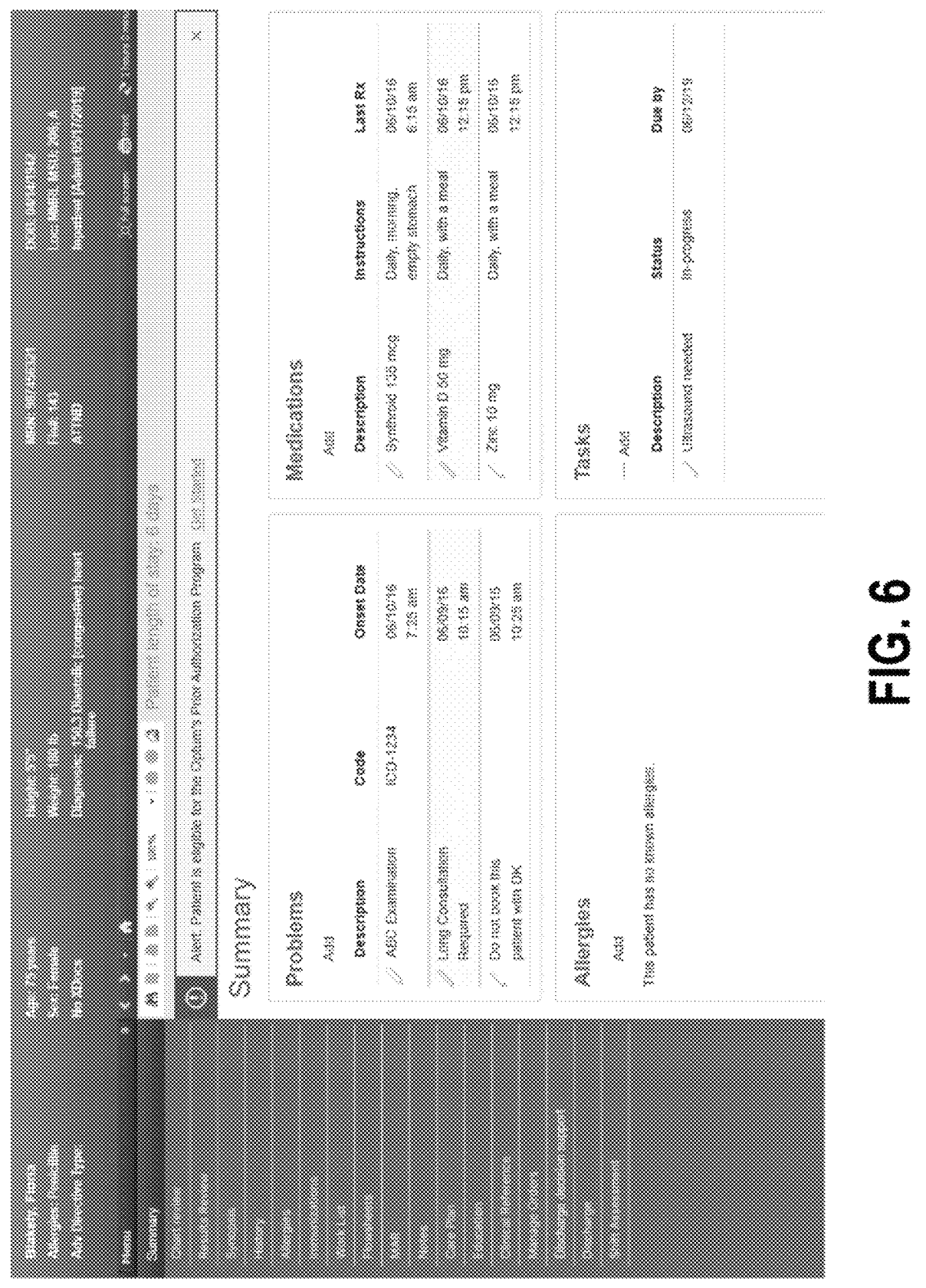

As indicated at FIG. 6, access to the prior authorization system may be provided through a banner presented to a user on a patient summary page of an EMR system and/or another management system (e.g., a healthcare facility management system, a patient management system, and/or the like). As shown in the illustrated example of FIG. 6, access to the prior authorization system may be optional, and may be made available to a user only upon an initial determination by the analytic computing entity 65 that the functional data and/or the current claim data indicates that an automatically generated prior authorization approval may be available. In certain embodiments, determinations of recommended post-acute care options and/or recommended providers for the post-acute care may be generated by the analytic computing entity 65 (as discussed above) in real-time, prior to providing a banner indicating availability of the prior authorization system.

As indicated in FIG. 6, the banner (or other indication) providing access to the prior authorization system may be embodied as an interactive graphical user interface element that may be selected by a user to access additional user interface screens relevant to the prior authorization system. For example, selecting the interactive graphical user interface element may cause the analytic computing entity 65 to provide the user with a user interface screen such as that shown in FIG. 7. In the illustrated example of FIG. 7, the graphical user interface screen may provide a summary of the patient's current claim, and may request user input confirming one or more additional aspects of the patient's current claim. Access to later user interface screens may not be provided until the user provides all relevant and requested user input.

Figure 8:
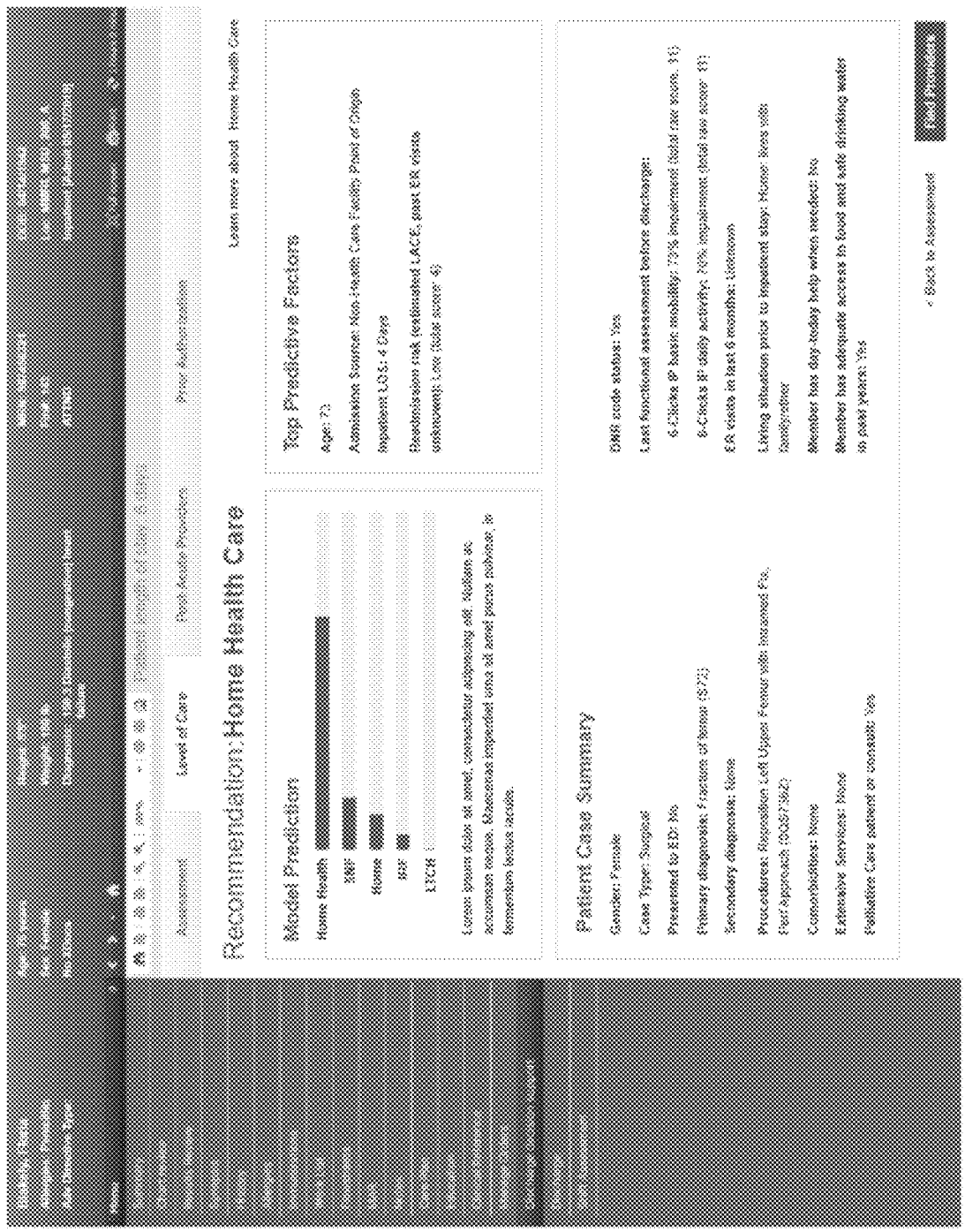

Selecting an appropriate graphical user interface element (e.g., a selectable button identified for navigating to another graphical user interface providing recommendations for a post-acute care option for the patient), causes the analytic computing entity 65 to provide a graphical user interface such as that shown in FIG. 8 to the user. FIG. 8 provides an example graphical user interface providing a recommendation for a post-acute care option for a patient. As noted above, generation of the recommendation for the post-acute care option may be completed by the analytic computing entity 65 prior to providing the graphical interface screen such as that shown in FIG. 8 to the user (e.g., determinations of a recommended post-acute care option may be generated prior to and/or while displaying a summary page, such as that shown in FIG. 6). As shown in the example graphical user interface of FIG. 8, the analytic computing entity 65 may be configured to generate data identifying a most-recommended post-acute care option, as well as data identifying the analytical results associated with other post-acute care options. As just one example, the analytic computing entity 65 may be configured to generate a bar graph illustrating the relative predictive recommendation scores for each of the plurality of displayed post-acute care options. The graphical user interface may additionally comprise data indicative of one or more portions of functional data and/or current claim data that strongly correlated to the identification of a particular recommendation for post-acute care options. In the illustrated example of FIG. 8, Home Health is identified as the recommendation for the particular patient (as indicated by the large summary text at the top of the graphical user interface, as well as by the relative model prediction scores as reflected by the illustrated bar graph). As shown in the illustrated example, Home Health was identified by the analytic computing entity 65 based at least partially on the patient's age, the patient's admission source, the patient's inpatient Length of Stay (LOS), and the readmission risk score. Although other portions of the functional data and/or the current claim data may have contributed to the overall score, the analytic computing entity 65 determined that these four factors contributed more than other factors to the recommendation of Home Health.

Moreover, as illustrated in FIG. 8, the displayed graphical user interface may additionally comprise patient summary data for the user's review. In the event that a user does not agree with the recommended post-acute care option, the provider may exit the prior authorization system, for example, via a displayed interactive graphical user interface element. However, if the user agrees with the recommended post-acute care, the provider may select an interactive graphical user interface element to "Find Providers" (or other similar indicator).

Figure 9:
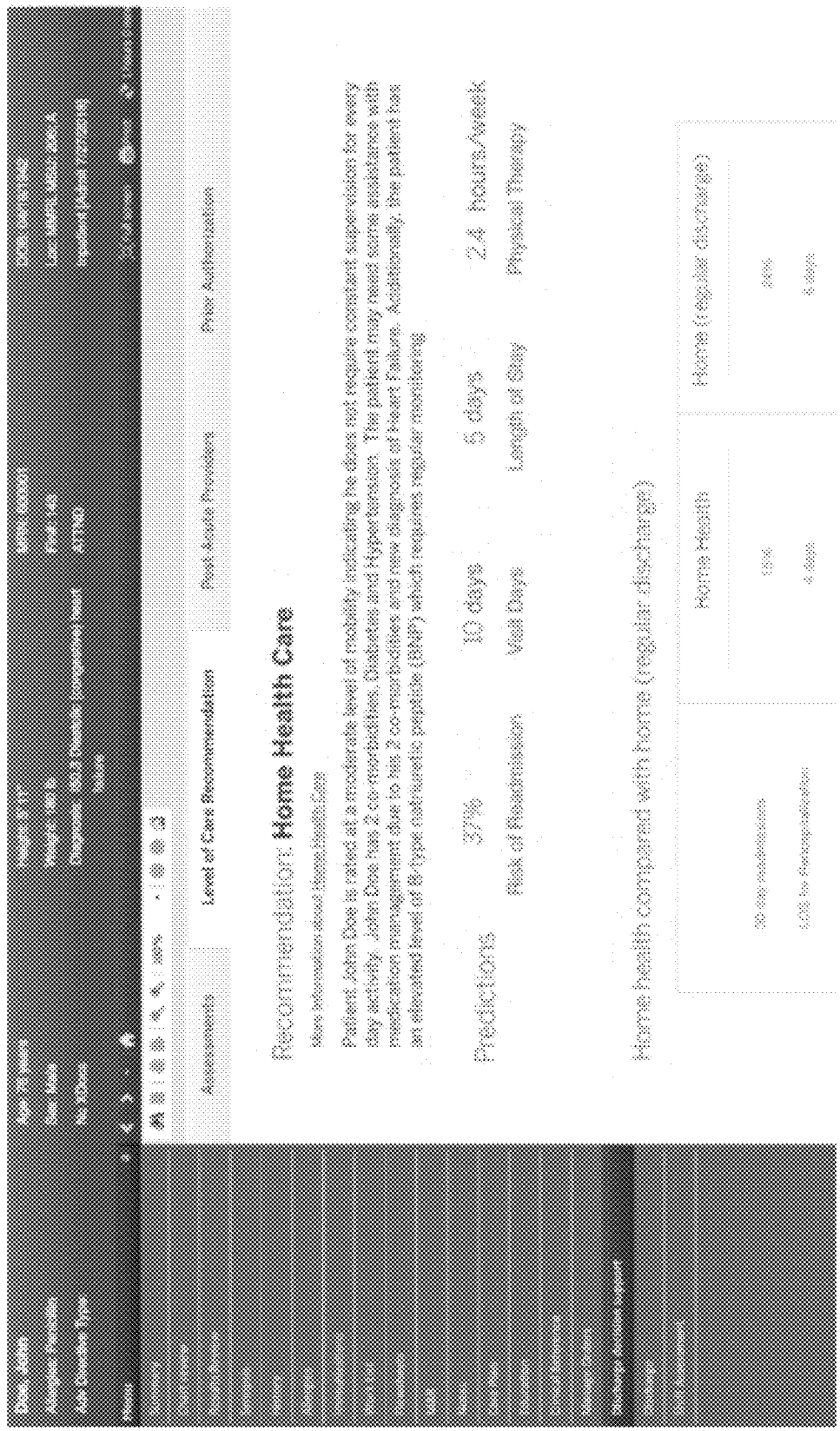

FIG. 9 provides an alternative example of a potential graphical user interface that may be provided to a user to display a recommendation for a particular post-acute care option. As illustrated in FIG. 9, the graphical user interface element may provide numerical data indicative of predictions of outcomes of the recommended post-acute care option, as well as numerical data comparing the recommended post-acute care option with other, non-recommended post-acute care options.

Figure 10:
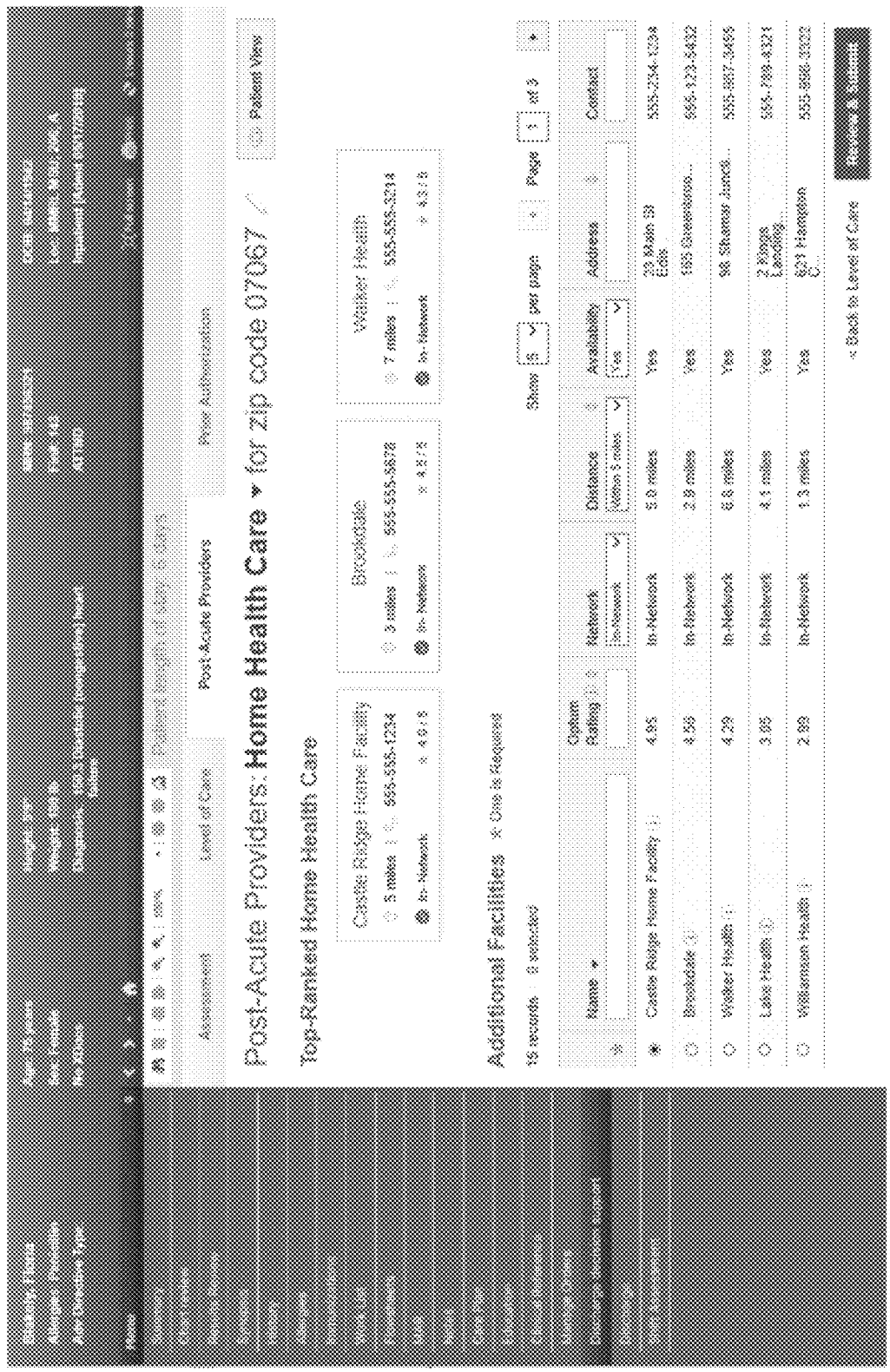

Upon selection of the graphical user interface element to find providers for the recommended post-acute care option, the analytic computing entity 65 may provide a graphical user interface such as that shown in FIG. 10 to a user. The analytic computing entity 65 may provide the user with a graphical listing of available providers capable of providing the recommended post-acute care to the patient. As noted above, the listing of available providers may be generated in real-time and/or before display of the graphical user interface similar to FIG. 10. As shown in FIG. 10, the analytic computing entity 65 may identify one or more recommended and/or "top-ranked" providers for providing the recommended post-acute care for the patient, as well as one or more additional providers that may selected for providing the post-acute care option selected. As shown in FIG. 10, various provider data may be displayed within the graphical user interface, such as the distance to the provider from the patient's location (or another selected location), the name of the provider, contact data for the provider, and/or the like.

In certain embodiments, the analytic computing entity 65 may be configured to generate a prior authorization approval upon selection of any of a subset of displayed providers (e.g., only the top ranked providers), but not other providers. In other embodiments, the analytic computing entity 65 may be configured to generate a prior authorization approval upon selection of any of the displayed providers. In the event the user does not wish to utilize any of the displayed providers, the user may exit the prior authorization system to submit a prior authorization request under more traditional methods.

Upon selection of a particular provider for providing the selected post-acute care option, the user may be enabled to select an interactive graphical user interface element to review the prior authorization approval and submit the same to the payer and/or the selected provider.

Once the user is satisfied with the post-acute care option and/or provider selected, the user selects the interactive graphical user interface element to generate the prior authorization approval. As noted above, generation of the prior authorization approval may comprise determining data and/or data formatting requirements for the payer, determining appropriate locations to transmit various data, generation of a prior authorization approval unique identifier, and/or the like. Ultimately, the analytic computing entity 65 provides the user with a graphical user interface similar to that shown in FIG. 11, providing an indication that the prior authorization has been approved, providing the prior authorization approval unique identifier, providing an indication of the post-acute care option provided, and providing an indication of the prior selected to provide the post-acute care.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for identifying contributing factors of a recommendation generated by a machine-learning recommendation engine, the method comprising:
   receiving functional data corresponding to a patient, wherein the functional data is linked with a patient medical record and wherein the functional data comprises a plurality of functional data entries;
   executing at least one machine-learning model to generate a recommendation for the patient based at least in part on functional data entries of the functional data;
   generating entry weights for one or more of the plurality of functional data entries within the functional data, wherein the entry weights are indicative of a relative importance of a corresponding functional data entry for generating the recommendation for the patient; and
   generating a graphical user interface identifying the recommendation and one or more of the plurality of functional data entries having corresponding entry weights satisfying a display criteria.

2. The computer-implemented method of claim 1, wherein executing at least one machine-learning model to generate a recommendation for the patient based at least in part on functional data comprises:
   executing a first machine-learning model to determine one or more options for the patient, wherein the first machine-learning model is trained to determine the one or more options according to common option utilization; and
   executing a second machine-learning model to determine rates of negative outcomes associated with the one or more options, wherein the second machine-learning model is trained via a negative training data set to avoid negative outcomes associated with one or more of the options.

3. The computer-implemented method of claim 2, further comprising:
   executing an opportunity-based machine-learning model configured to determine one or more alternative options based at least in part on the functional data, wherein the one or more alternative options each embody a minority-utilized option for the patient; and
   wherein generating a graphical user interface further comprises generating a graphical user interface identifying the one or more alternative options.

4. The computer-implemented method of claim 3, wherein determining one or more alternative options comprises:
   identifying one or more options for the patient;
   identifying an outcome for each of the one or more options for the patient;
   identifying an option subset comprising one or more options determined to satisfy utilization criteria;
   identifying an outcome for each of one or more options for the patient; and
   determining one or more alternative options comprising options selected from the option subset determined to have an outcome at least matching the outcome for the recommendation.

5. The computer-implemented method of claim 2, wherein the second machine-learning model is trained via negative training data to avoid options having negative outcomes.

6. The computer-implemented method of claim 1, wherein the recommendation comprises a post-acute care recommendation.

7. The computer-implemented method of claim 1, wherein the machine-learning model is embodied as an unsupervised training machine-learning model.

8. The computer-implemented method of claim 1, further comprising:
   receiving user input selecting the recommendation, wherein the recommendation is embodied as a post-acute care option;
   generating a prior-authorization approval for the recommendation; and
   transmitting data indicative of the prior-authorization approval to one or more computing entities.

9. An apparatus comprising at least one processor and at least one non-transitory memory comprising program code, wherein the at least one non-transitory memory and the program code are configured to, with the at least one processor, cause the apparatus to:
   receive functional data corresponding to a patient, wherein the functional data is linked with a patient medical record and wherein the functional data comprises a plurality of functional data entries;
   execute at least one machine-learning model to generate a recommendation for the patient based at least in part on functional data entries of the functional data;
   generate entry weights for one or more of the plurality of functional data entries within the functional data, wherein the entry weights are indicative of a relative importance of a corresponding functional data entry for generating the recommendation for the patient; and
   generate a graphical user interface identifying the recommendation and one or more of the plurality of functional data entries having corresponding entry weights satisfying a display criteria.

10. The apparatus of claim 9, wherein executing at least one machine-learning model to generate a recommendation for the patient based at least in part on functional data comprises:
    executing a first machine-learning model to determine one or more options for the patient, wherein the first machine-learning model is trained to determine the one or more options according to common option utilization; and
    executing a second machine-learning model to determine rates of negative outcomes associated with the one or more options, wherein the second machine-learning model is trained via a negative training data set to avoid negative outcomes associated with one or more of the options.

11. The apparatus of claim 10, wherein the at least one non-transitory memory and the program code are further configured to, with the at least one processor, cause the apparatus to:
execute an opportunity-based machine-learning model configured to determine one or more alternative options based at least in part on the functional data, wherein the one or more alternative options each embody a minority-utilized option for the patient; and
wherein generating a graphical user interface further comprises generating a graphical user interface identifying the one or more alternative options.

12. The apparatus of claim 11, wherein determining one or more alternative options comprises:
identifying one or more options for the patient;
identifying an outcome for each of the one or more options for the patient;
identifying an option subset comprising one or more options determined to satisfy utilization criteria;
identifying an outcome for each of one or more options for the patient; and
determining one or more alternative options comprising options selected from the option subset determined to have an outcome at least matching the outcome for the recommendation.

13. The apparatus of claim 10, wherein the second machine-learning model is trained via negative training data to avoid options having negative outcomes.

14. The apparatus of claim 9, wherein the recommendation comprises a post-acute care recommendation.

15. The apparatus of claim 9, wherein the machine-learning model is embodied as an unsupervised training machine-learning model.

16. The apparatus of claim 9, wherein the at least one non-transitory memory and the program code are further configured to, with the at least one processor, cause the apparatus to:
receive user input selecting the recommendation, wherein the recommendation is embodied as a post-acute care option;
generate a prior-authorization approval for the recommendation; and
transmit data indicative of the prior-authorization approval to one or more computing entities.

17. A non-transitory computer storage medium comprising instructions configured to cause one or more processors to:
receive functional data corresponding to a patient, wherein the functional data is linked with a patient medical record and wherein the functional data comprises a plurality of functional data entries;
execute at least one machine-learning model to generate a recommendation for the patient based at least in part on functional data entries of the functional data;
generate entry weights for one or more of the plurality of functional data entries within the functional data, wherein the entry weights are indicative of a relative importance of a corresponding functional data entry for generating the recommendation for the patient; and
generate a graphical user interface identifying the recommendation and one or more of the plurality of functional data entries having corresponding entry weights satisfying a display criteria.

18. The non-transitory computer storage medium of claim 17, further comprising instructions configured to cause the one or more processors to:
executing a first machine-learning model to determine one or more options for the patient, wherein the first machine-learning model is trained to determine the one or more options according to common option utilization; and
executing a second machine-learning model to determine rates of negative outcomes associated with the one or more options, wherein the second machine-learning model is trained via a negative training data set to avoid negative outcomes associated with one or more of the options.

19. The non-transitory computer storage medium of claim 18, further comprising instructions configured to cause the one or more processors to:
execute an opportunity-based machine-learning model configured to determine one or more alternative options based at least in part on the functional data, wherein the one or more alternative options each embody a minority-utilized option for the patient; and
wherein generating a graphical user interface further comprises generating a graphical user interface identifying the one or more alternative options.

20. The non-transitory computer storage medium of claim 19, wherein determining one or more alternative options comprises:
identifying one or more options for the patient;
identifying an outcome for each of the one or more options for the patient;
identifying an option subset comprising one or more options determined to satisfy utilization criteria;
identifying an outcome for each of one or more options for the patient; and
determining one or more alternative options comprising options selected from the option subset determined to have an outcome at least matching the outcome for the recommendation.

21. The non-transitory computer storage medium of claim 18, wherein the second machine-learning model is trained via negative training data to avoid options having negative outcomes.

22. The non-transitory computer storage medium of claim 17, wherein the recommendation comprises a post-acute care recommendation.

23. The non-transitory computer storage medium of claim 17, wherein the machine-learning model is embodied as an unsupervised training machine-learning model.

24. The non-transitory computer storage medium of claim 17, further comprising instructions configured to cause the one or more processors to:
receive user input selecting the recommendation, wherein the recommendation is embodied as a post-acute care option;
generate a prior-authorization approval for the recommendation; and
transmit data indicative of the prior-authorization approval to one or more computing entities.

* * * * *